(12) United States Patent
Scherer et al.

(10) Patent No.: US 7,820,401 B2
(45) Date of Patent: Oct. 26, 2010

(54) COLLAGEN VI AND CANCER

(75) Inventors: Philipp E. Scherer, Southlake, TX (US); Puneeth Iyengar, Houston, TX (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 241 days.

(21) Appl. No.: 11/660,181

(22) PCT Filed: Aug. 11, 2005

(86) PCT No.: PCT/US2005/028687

§ 371 (c)(1),
(2), (4) Date: Mar. 12, 2008

(87) PCT Pub. No.: WO2006/023382

PCT Pub. Date: Mar. 2, 2006

(65) Prior Publication Data

US 2009/0011438 A1   Jan. 8, 2009

Related U.S. Application Data

(60) Provisional application No. 60/603,579, filed on Aug. 23, 2004.

(51) Int. Cl.
*G01N 33/574* (2006.01)

(52) U.S. Cl. ........................ 435/7.23; 435/7.1
(58) Field of Classification Search .............. None
See application file for complete search history.

(56) References Cited

U.S. PATENT DOCUMENTS

2002/0072503 A1 * 6/2002 Xu et al. .................. 514/44
2004/0029114 A1 * 2/2004 Mack et al. ................ 435/6

OTHER PUBLICATIONS

Sherman-Baust et al, Cancer Cell, Apr. 2003, 3:377-386.*

* cited by examiner

*Primary Examiner*—Misook Yu
*Assistant Examiner*—Mark Halvorson
(74) *Attorney, Agent, or Firm*—Amster, Rothstein & Ebenstein LLP

(57) ABSTRACT

Methods of determining whether a cancer is progressing by measuring surface-bound collagen VIα3 are provided. Also provided are methods of identifying hyperplasia in a tissue by measuring surface-bound collagen VIα3. Additionally, methods of identifying carcinoma in a tissue by measuring surface-bound collagen VIα3 are provided. Further provided are methods of imaging carcinoma in a tissue by staining the tissue with a specific binding partner to collagen VIα3. Methods of treating a cancer by preventing binding of collagen VIα3 onto cells of the cancer are additionally provided.

20 Claims, 10 Drawing Sheets

FIG. 1 (A-C)
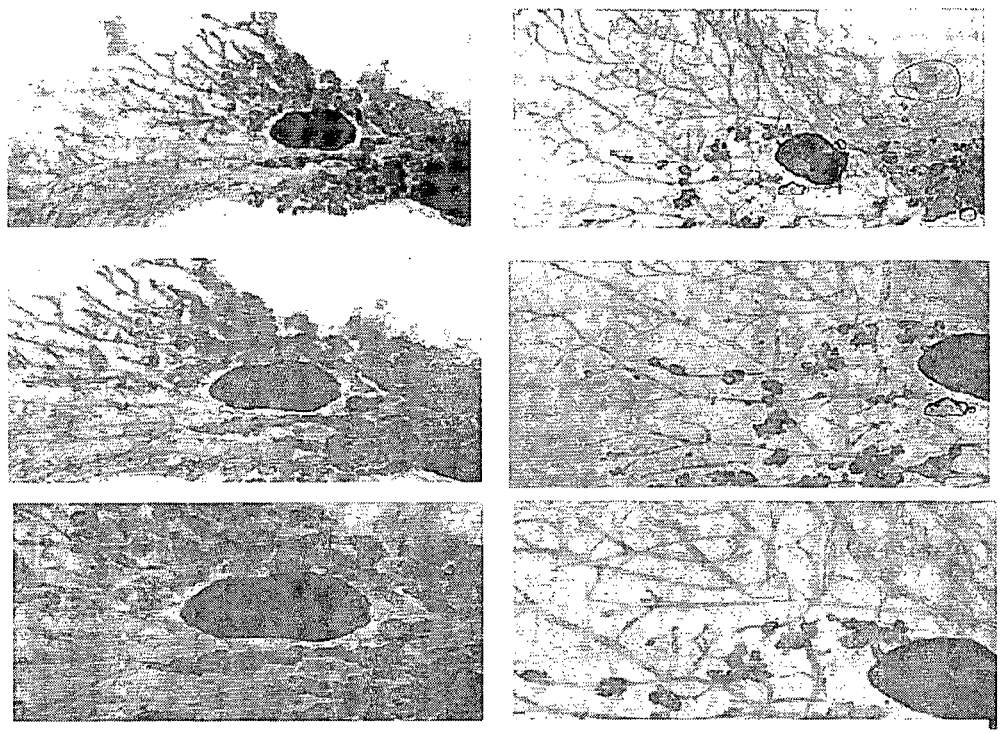
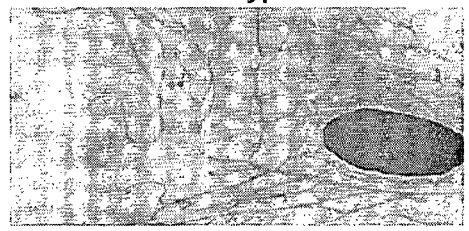
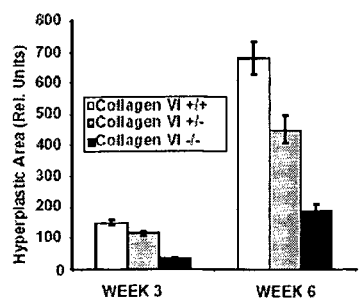
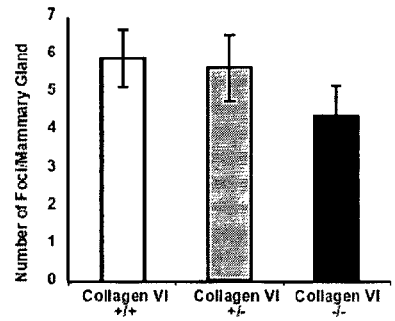

FIG. 1 (D-G)
D
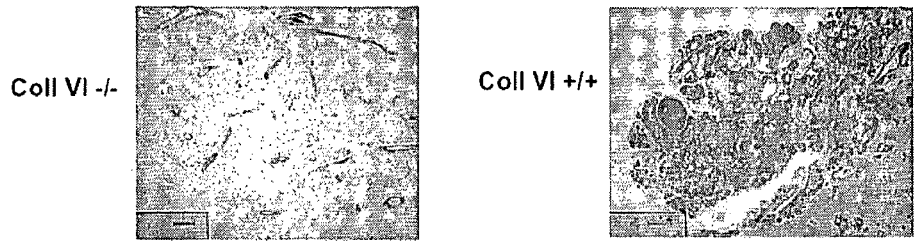
E
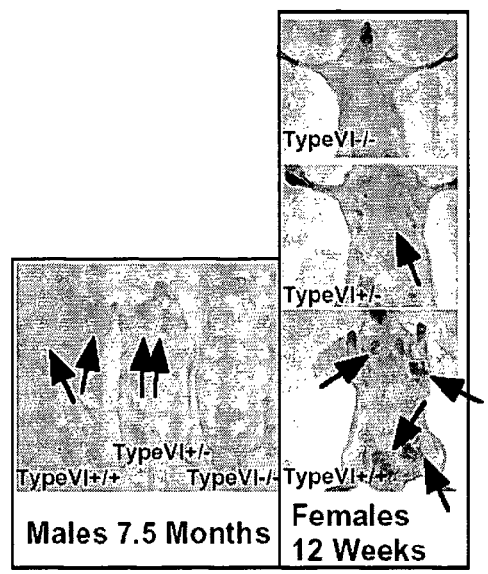
F
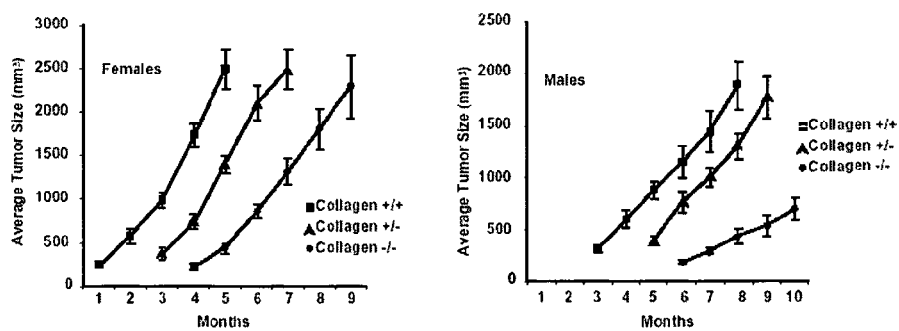
G
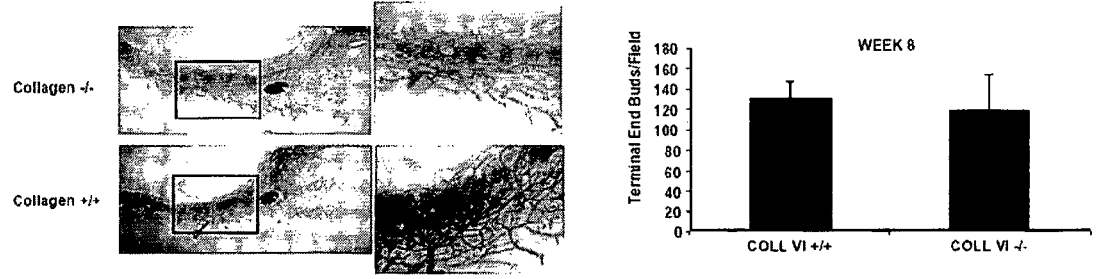

Stain for Metallothionein

FIG. 4
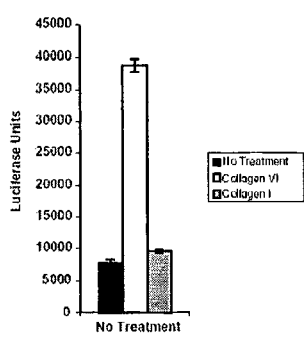
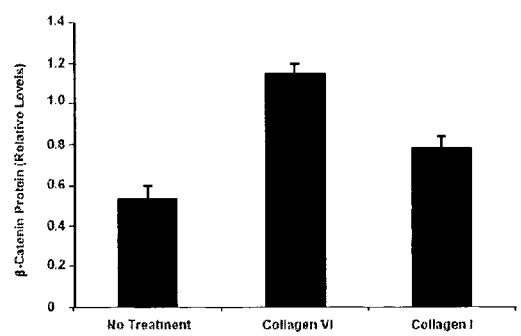
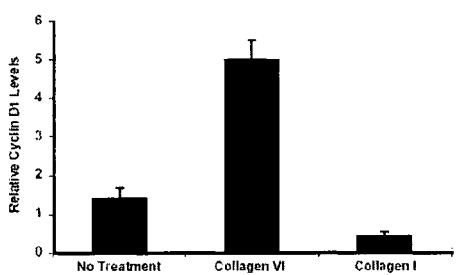

FIG. 6
A
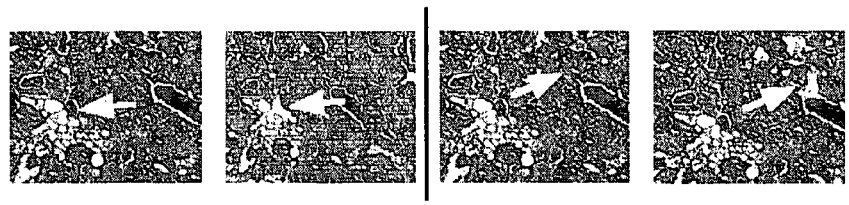
B
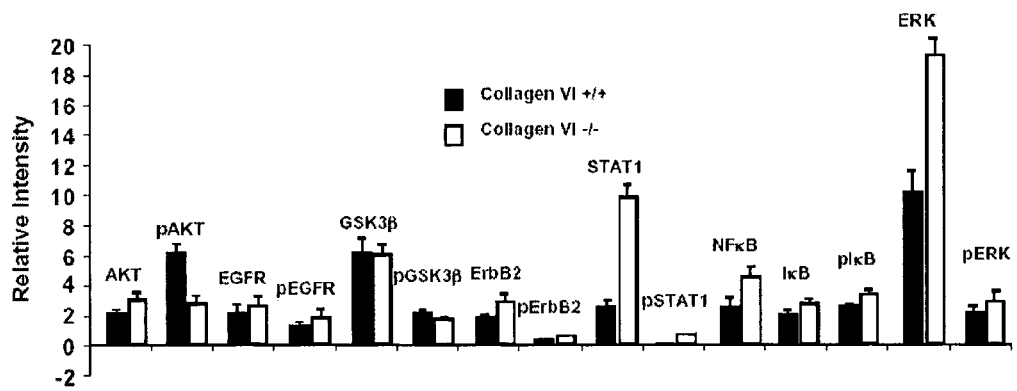
C
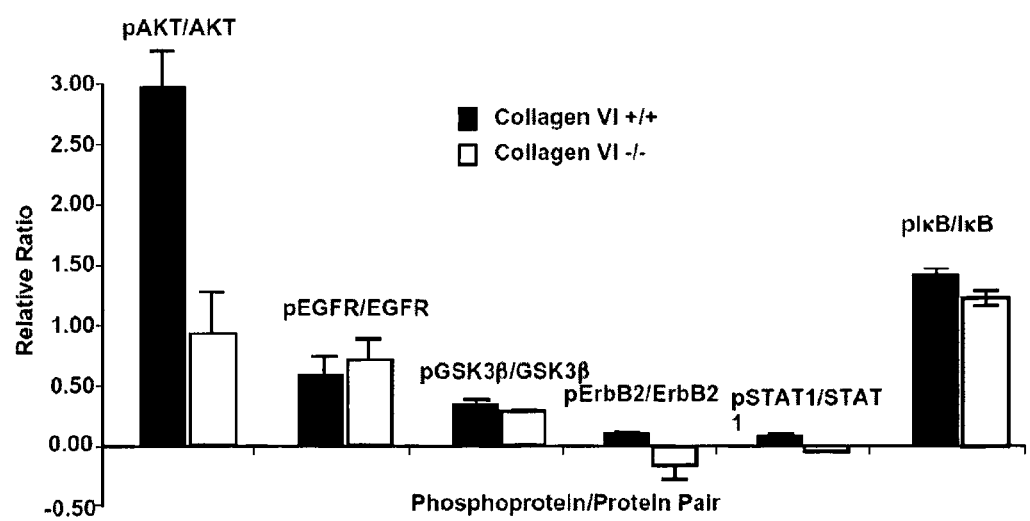

FIG. 9 (cont.)
F
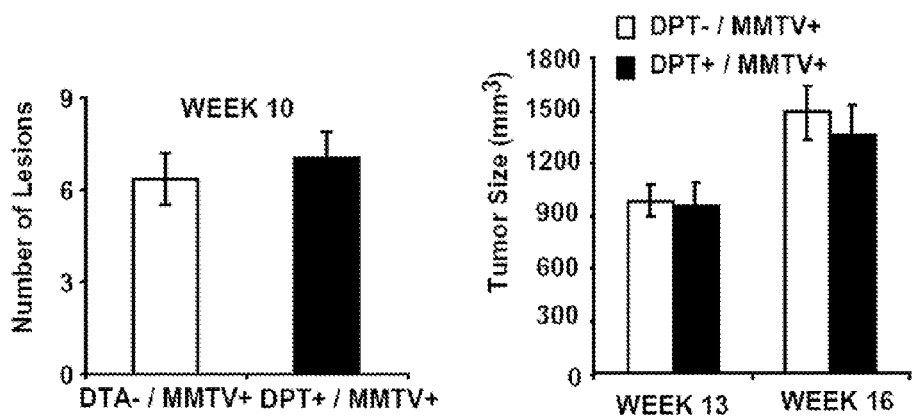
G
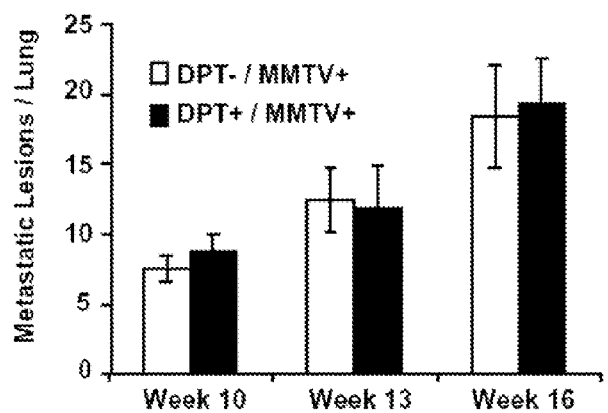
H
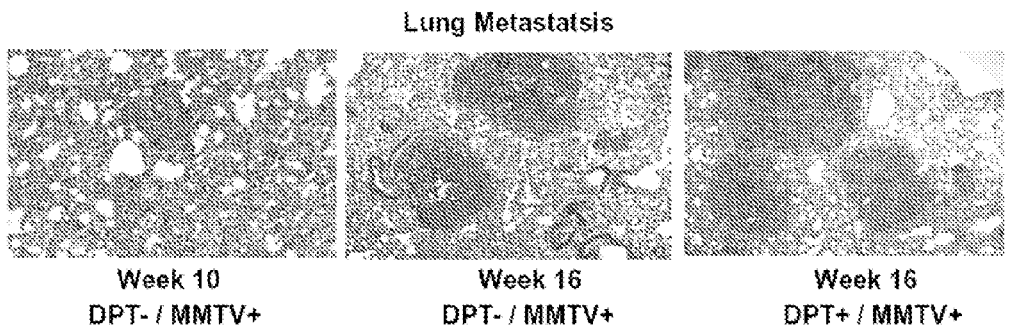

COLLAGEN VI AND CANCER

CROSS-REFERENCE TO RELATED APPLICATION

This application is a U.S. national phase of PCT Application No. PCT/US2005/028687 filed Aug. 11, 2005, which claims the benefit of U.S. Provisional Application No. 60/603,579, filed Aug. 23, 2004.

STATEMENT REGARDING FEDERALLY SPONSORED RESEARCH OR DEVELOPMENT

The present invention was supported by Grant No. T32-GM07288 awarded by the National Institutes of Health. As such, the U.S. Government has certain rights in the invention.

BACKGROUND (1) Field of the Invention

The present invention generally relates to factors influencing the proliferation of cancer. More specifically, the invention relates to methods for detecting or treating cancer based on the newly recognized ability of cancer cell surface collagen VIα3 to enhance the proliferation of cancer cells.

(2) Description of the Related Art

REFERENCES CITED

Aigner, T., Hambach, L., Soder, S., Schlotzer-Schrehardt, U., and Poschl, E. (2002). The C5 domain of Col6A3 is cleaved off from the Col6 fibrils immediately after secretion. Biochem Biophys Res Commun 290, 743-748.

Albanese, C., Wu, K., D'Amico, M., Jarrett, C., Joyce, D., Hughes, J., Hulit, J., Sakamaki, T., Fu, M., Ben-Ze'ev, A., et al. (2003). IKKalpha regulates mitogenic signaling through transcriptional induction of cyclin D1 via Tcf. Mol Biol Cell 14, 585-599.

Baldock, C., Sherratt, M. J., Shuttleworth, C. A., and Kielty, C. M. (2003). The supramolecular organization of collagen VI microfibrils. J Mol Biol 330, 297-307.

Berking, C., Takemoto, R., Schaider, H., Showe, L., Satyamoorthy, K., Robbins, P., and Herlyn, M. (2001). Transforming growth factor-beta1 increases survival of human melanoma through stroma remodeling. Cancer Res 61, 8306-8316.

Bonaldo, P., Braghetta, P., Zanetti, M., Piccolo, S., Volpin, D., and Bressan, G. M. (1998). Collagen VI deficiency induces early onset myopathy in the mouse: an animal model for Bethlem myopathy. Hum Mol Genet 7, 2135-2140.

Boudny, V., and Kovarik, J. (2002). JAK/STAT signaling pathways and cancer. Janus kinases/signal transducers and activators of transcription. Neoplasma 49, 349-355.

Cardiff, R. D., Anver, M. R., Gusterson, B. A., Hennighausen, L., Jensen, R. A., Merino, M. J., Rehm, S., Russo, J., Tavassoli, F. A., Wakefield, L. M., et al. (2000). The mammary pathology of genetically engineered mice: the consensus report and recommendations from the Annapolis meeting. Oncogene 19, 968-988.

Chekenya, M., Enger, P. O., Thorsen, F., Tysnes, B. B., Al-Sarraj, S., Read, T. A., Furmanek, T., Mahesparan, R., Levine, J. M., Butt, A. M., et al. (2002a). The glial precursor proteoglycan, NG2, is expressed on tumour neovasculature by vascular pericytes in human malignant brain tumours. Neuropathol Appl Neurobiol 28, 367-380.

Chekenya, M., Hjelstuen, M., Enger, P. O., Thorsen, F., Jacob, A. L., Probst, B., Haraldseth, O., Pilkington, G., Butt, A., Levine, J. M., and Bjerkvig, R. (2002b). NG2 proteoglycan promotes angiogenesis dependent tumor growth in CNS by sequestering angiostatin. Faseb J 16, 586-588.

Chekenya, M., Rooprai, H. K., Davies, D., Levine, J. M., Butt, A. M., and Pilkington, G. J. (1999). The NG2 chondroitin sulfate proteoglycan: role in malignant progression of human brain tumours. Int J Dev Neurosci 17, 421-435.

Chen, Z. J., Negra, M., Levine, A., Ughrin, Y., and Levine, J. M. (2002a). Oligodendrocyte precursor cells: Reactive cells that inhibit axon growth and regeneration. J Neurocytol 31, 481-495.

Chen, Z. J., Ughrin, Y., and Levine, J. M. (2002b). Inhibition of axon growth by oligodendrocyte precursor cells. Mol Cell Neurosci 20, 125-139.

Dadachova, E., and Mirzadeh, S. (1997). The role of tin in the direct labelling of proteins with Rhenium-188. Nucl Med Biol 24, 605-608.

Elenbaas, B., and Weinberg, R. A. (2001). Heterotypic signaling between epithelial tumor cells and fibroblasts in carcinoma formation. Exp Cell Res 264, 169-184.

Elliott, B. E., Tam, S. P., Dexter, D., and Chen, Z. Q. (1992). Capacity of adipose tissue to promote growth and metastasis of a murine mammary carcinoma: effect of estrogen and progesterone. Int J Cancer 51, 416-424.

Engelman, J. A., Lisanti, M. P., and Scherer, P. E. (1998). Specific inhibitors of p38 MAP Kinase block 3T3-L1 Adipogenesis. J Biol Chem 273, 32111-32120.

Fang, X., Burg, M. A., Barritt, D., Dahlin-Huppe, K., Nishiyama, A., and Stallcup, W. B. (1999). Cytoskeletal reorganization induced by engagement of the NG2 proteoglycan leads to cell spreading and migration. Mol Biol Cell 10, 3373-3387.

Flanagan, L., Van Weelden, K., Ammerman, C., Ethier, S. P., and Welsh, J. (1999). SUM-159PT cells: a novel estrogen independent human breast cancer model system. Breast Cancer Res Treat 58, 193-204.

Giles, R. H., van Es, J. H., and Clevers, H. (2003). Caught up in a Wnt storm: Wnt signaling in cancer. Biochim Biophys Acta 1653, 1-24.

Gladson, C. L. (1999). The extracellular matrix of gliomas: modulation of cell function. J Neuropathol Exp Neurol 58, 1029-1040.

Guy, C. T., Cardiff, R. D., and Muller, W. J. (1992). Induction of maimmary tumors by expression of polyomavirus middle T oncogene: a transgenic mouse model for metastatic disease. Mol Cell Biol 12, 954-961.

Howell, S. J., and Doane, K. J. (1998). Type VI collagen increases cell survival and prevents anti-beta 1 integrin-mediated apoptosis. Exp Cell Res 241, 230-241.

Irwin, W. A., Bergamin, N., Sabatelli, P., Reggiani, C., Megighian, A., Merlini, L., Braghetta, P., Columbaro, M., Volpin, D., Bressan, G. M., et al. (2003). Mitochondrial dysfunction and apoptosis in myopathic mice with collagen VI deficiency. Nat Genet 35, 367-371.

Iyengar, P., Combs T. P., Shah, S. J., Gouon-Evans, V., Pollard, J. W., Albanese, C., Flanagan, L., Tenniswood, M. P., Guha, C., Lisanti, M. P., et al. (2003). Adipocyte Secreted Factors Synergistically Promote Mammary Tumorigenesis Through Induction of anti-Apoptotic Transcriptional Programs and Proto-Oncogene Stabilization. Oncogene 22, 6408-6423.

Jobsis, G. J., Bolhuis, P. A., Boers, J. M., Baas, F., Wolterman, R. A., Hensels, G. W., and de Visser, M. (1996a). Genetic localization of Bethlem myopathy. Neurology 46, 779-782.

Jobsis, G. J., Keizers, H., Vreijling, J. P., de Visser, M., Speer, M. C., Wolterman, R. A., Baas, F., and Bolhuis, P. A.

(1996b). Type VI collagen mutations in Bethlem myopathy, an autosomal dominant myopathy with contractures. Nat Genet 14, 113-115.

Klausner, R. D. (2002). The fabric of cancer cell biology-Weaving together the strands. Cancer Cell 1, 3-10.

Lin, E. Y., Jones, J. G., Li, P., Zhu, L., Whitney, K. D., Muller, W. J., and Pollard, J. W. (2003). Progression to malignancy in the polyoma middle T oncoprotein mouse breast cancer model provides a reliable model for human diseases. Am J Pathol 163, 2113-2126.

Lin, E. Y., Nguyen, A. V., Russell, R. G., and Pollard, J. W. (2001). Colony-stimulating factor 1 promotes progression of mammary tumors to malignancy. J Exp Med 193, 727-740.

Martin, S., Levine, A. K., Chen, Z. J., Ughrin, Y., and Levine, J. M. (2001). Deposition of the NG2 proteoglycan at nodes of Ranvier in the peripheral nervous system. J Neurosci 21, 8119-8128.

Michaelson, J. S., and Leder, P. (2001). beta-catenin is a downstream effector of Wnt-mediated tumorigenesis in the mammary gland. Oncogene 20, 5093-5099.

Rajala, M. W., and Scherer, P. E. (2003). Minireview: The adipocyte—at the crossroads of energy homeostasis, inflammation, and atherosclerosis. Endocrinology 144, 3765-3773.

Ross, S. R., Graves, R. A., and Spiegelman, B. M. (1993). Targeted expression of a toxin gene to adipose tissue: transgenic mice resistant to obesity. Genes Dev 7, 1318-1324.

Ruhl, M., Sahin, E., Johannsen, M., Somasundaram, R., Manski, D., Riecken, E. O., and Schuppan, D. (1999). Soluble collagen VI drives serum-starved fibroblasts through S phase and prevents apoptosis via down-regulation of Bax. J Biol Chem 274, 34361-34368.

Scherer, P. E., Bickel, P. E., Kotler, M., and Lodish, H. F. (1998). Subtractive antibody screening: A new method to clone cell-specific secreted and surface proteins. Nature Biotechnol 16, 581-586.

Scherer, P. E., Lisanti, M. P., Baldini, G., Sargiacomo, M., Corley-Mastick, C., and Lodish, H. F. (1994). Induction of Caveolin during Adipogenesis and Association of GLUT4 with Caveolin-rich vesicles. J Cell Biol 127, 1233-1243.

Sherman-Baust, C. A., Weeraratna, A. T., Rangel, L. B., Pizer, E. S., Cho, K. R., Schwartz, D. R., Shock, T., and Morin, P. J. (2003). Remodeling of the extracellular matrix through overexpression of collagen VI contributes to cisplatin resistance in ovarian cancer cells. Cancer Cell 3, 377-386.

Speer, M. C., Tandan, R., Rao, P. N., Fries, T., Stajich, J. M., Bolhuis, P. A., Jobsis, G. J., Vance, J. M., Viles, K. D., Sheffield, K., et al. (1996). Evidence for locus heterogeneity in the Bethlem myopathy and linkage to 2q37. Hum Mol Genet 5, 1043-1046.

St Croix, B., Rago, C., Velculescu, V., Traverso, G., Romans, K. E., Montgomery, E., Lal, A., Riggins, G. J., Lengauer, C., Vogelstein, B., and Kinzler, K. W. (2000). Genes expressed in human tumor endothelium. Science 289, 1197-1202.

Ughrin, Y. M., Chen, Z. J., and Levine, J. M. (2003). Multiple regions of the NG2 proteoglycan inhibit neurite growth and induce growth cone collapse. J Neurosci 23, 175-186.

Vogel, W. F. (2001). Collagen-receptor signaling in health and disease. Eur J Dermatol 11, 506-514. Wiseman, B. S., and Werb, Z. (2002). Stromal effects on mammary gland development and breast cancer. Science 296, 1046-1049.

Wang, W., Wyckoff, J. B., Frohlich, V. C., Oleynikov, Y., Huttelmaier, S., Zavadil, J., Cermak, L., Bottinger, E. P., Singer, R. H., White, J. G., et al. (2002). Single cell behavior in metastatic primary mammary tumors correlated with gene expression patterns revealed by molecular profiling. Cancer Res 62, 6278-6288.

The interactions between malignant ductal epithelial cells and the surrounding stromal cells play a critical role in breast tumorigenesis and progression (Elenbaas and Weinberg, 2001; Klausner, 2002; Wiseman and Werb, 2002). Myelofibroblasts, macrophages, fibroblasts and adipocytes have been demonstrated to interact with breast cancer cells (Iyengar et al., 2003; Lin et al., 2001). The adipocyte is one of the predominant stromal cell types in the microenvironment of breast tissue as well as in bone marrow, an area frequently fostering metastases during breast cancer progression. A supportive role of adipocytes for tumor growth has previously been demonstrated by co-injection of tumor cells with adipocytes (Elliott et al., 1992), and many more studies have further elaborated on the vital role of tumor-stromal interactions for the development and progression of cancer.

The adipocyte is a potent source of signaling molecules, several of which are uniquely produced in this cell type (reviewed in (Rajala and Scherer, 2003)). We have previously shown that type VI collagen is upregulated during murine breast tumor progression (Iyengar et al., 2003). Type VI collagen, while expressed by a number of other cell types, is abundantly produced and secreted by adipocytes. Our earlier studies have shown that adipose tissue represents the single most abundant source of collagen VI systemically (Scherer et al., 1998). Collagen VI is composed of three chains, $\alpha 1$, $\alpha 2$, and $\alpha 3$, which associate to form higher order complexes (Baldock et al., 2003). The three chains of collagen VI form intracellular heterotrimers that subsequently form higher order complexes of tetramers of trimers before being secreted. Collagen VI contributes essential functions to the local extracellular matrix environment by providing structural support for cells, enrichment of growth factors, cytokines and other ligands on cell surfaces, and can, in fact, assume itself important signaling effects (Vogel, 2001).

Increased stromal expression of collagen VI has been correlated with various aspects of tumorigenesis and malignant progression. Specifically, the $\alpha 3$ subunit of collagen VI is upregulated in the stroma surrounding colonic tumors compared to that surrounding normal tissue (St Croix et al., 2000). Exposure of fibroblasts to collagen VI promotes proliferation and upregulation of cyclin D1 (Ruhl et al., 1999). Collagen VI can also increase cell migration and invasion in cells expressing the NG2 chondroitin sulfate proteoglycan (CSPG)1 receptor (Fang et al., 1999). Furthermore, the protein inhibits apoptosis in a variety of cell types (Howell and Doane, 1998). TGFβ expressing melanoma cells induce collagen VI expression in mammary stroma, facilitating tumor progression and invasiveness (Berking et al., 2001). Most recently, increased collagen VI expression in the extracellular matrix has been associated with the promotion of chemoresistance in ovarian cancer cells (Sherman-Baust et al., 2003).

SUMMARY OF THE INVENTION

Accordingly, the inventors have discovered that levels of the carboxy-terminal domain of collagen VIα3, a proteolytic product of the full-length molecule, dramatically accumulates in murine and human breast cancer cells. When bound to the surface of carcinoma cells, the collagen VIα3 promotes survival and proliferation of the cells.

Thus, in some embodiments, the invention is directed to methods of determining whether a cancer is progressing. The methods comprise determining whether cells of the cancer have more surface-bound collagen VIα3 than cancer cells that are not progressing.

In other embodiments, the invention is directed to methods of identifying hyperplasia in a tissue. The methods comprise identifying epithelial cells of the tissue that have more surface-bound collagen VIα3 than epithelial cells not undergoing hyperplasia. In these embodiments, the identified epithelial cells are undergoing hyperplasia.

Additionally, the invention is directed to methods of identifying carcinoma in a tissue. The methods comprise identifying epithelial cells that have more surface-bound collagen VIα3 than normal epithelial cells. In these embodiments, the identified epithelial cells are carcinoma cells.

The invention is further directed to methods of imaging carcinoma in a tissue. The methods comprise staining the tissue with a specific binding partner to collagen VIα3, then imaging epithelial cells of the tissue to determine whether the binding partner specifically binds to the epithelial cells. The epithelial cells comprising the specific binding partner are carcinoma cells.

The invention is additionally directed to methods of treating a cancer. The methods comprise preventing binding of collagen VIα3 onto cells of the cancer.

BRIEF DESCRIPTION OF THE DRAWINGS

FIG. 1 is graphs, photographs and micrographs demonstrating that lack of collagen VI leads to a dramatic reduction in tumor growth. Panel A shows high level expression of collagen VI in adipose tissue with a whole mount analysis of early hyperplasia in 5-6 week old MMTV-PyMT transgenic mice in collagen VI (+/+) (left panels) or collagen VI (−/−) (right panels). Higher magnifications of the same images are shown from top to bottom. The panel at the bottom in the center shows a whole mount from a wildtype mouse that does not carry the MMTV-PyMT transgene. Panel B shows collagen VI dose-dependent reduction in hyperplastic foci size. Hyperplastic areas were quantitated at 3 and 6 weeks using NIH Image J Software to determine the relative areas covered by hyperplastic foci in collagen +/+ (white), collagen (+/−) (grey) and collagen (−/−) (black) mice in the background of the MMTV-PyMT antigen. Panel C shows that the number of hyperplastic foci does not significantly depend on collagen VI presence or absence in the MMTV-PyMT mouse. NIH Image J Software was used to quantitate the number of foci formed in the mammary glands of 3 week old in collagen +/+ (white), collagen (+/−) (grey) and collagen (−/−) (black) mice in the background of the MMTV-PyMT antigen. Panel D shows a representative H&E stain of a mammary section taken from CollVI−/−/PyMT+ and CollVI+/+/PyMT+ mice at 6 weeks of age. Note the lack of any major lesions in the absence of collagen VI, whereas the presence of collagen VI in the background of the MMTV-PyMT transgene displays the characteristic appearance of hyperplasias. Panel E shows the reduced tumor size in collagen VI (−/−) mice. Size differences in primary tumors for male mice at approximately 30 weeks of age (left panels) and female mice at 12 weeks of age (right panels). All mice carried the MMTV-PyMT transgene and either were collagen VI (+/+), collagen VI (+/−) or collagen VI (−/−). Panel F shows the quantitation of tumor sizes of female (left) or male (right) mice carrying the MMTV-PyMT transgene in the background of collagen VI (+/+) (squares), collagen VI (+/−) (triangles) or collagen VI (−/−) (circles) at different ages up to 9 months. A minimum of 10 mice was used for the determination of tumor size in all cases. Panel G shows that collagen VI does not play a major role in normal development of the ductal epithelium in a whole mount analysis of the 4th mammary gland of week 8 collagen −/− mice (top) and collagen VI +/+ mice (bottom). Low (left) and high (right) magnifications are shown (20× and 40×). The extent of terminal end bud development in the two mouse models was determined by counting the number of terminal end buds in equivalent distances from the lymph node in 3 mice from each genotype. Results are shown as the MEAN±SEM in all cases.

FIG. 4 is graphs and a photograph showing that collagen VI stabilizes β-catenin and cyclin D1. Panel A shows collagen VI mediated TCF/LEF induction. A TCF/LEF luciferase reporter construct was transfected into MCF-7 cells and luciferase activity was analyzed after treatment either were vehicle (PBS; black bars), collagen VI (30 μg/ml; white bars) or collagen 1 (30 μg/ml; gray bars) in DME-BSA. Panel B shows β-catenin stability after collagen exposure: MCF-7 cells were metabolically labeled and then chased in the presence of cycloheximide for 30 min, 1, and 2 hrs. The serum free medium used in the chase contained vehicle, collagen VI (30 μg/ml) or collagen 1 (30 μg/ml). After each time point, immunoprecipitations were performed for β-catenin and analyzed by SDS-PAGE followed by quantitation of β-catenin at each time point. The graph shows the ratio of β-catenin at 30 minutes compared to 2 hours as an indicator of β-catenin stability. Panel C shows cyclin D1 stability after collagen exposure. MCF-7 cells were exposed for 3 hours to vehicle, human collagen VI (30 μg/ml) or collagen I (30 μg/ml). Cells were then lysed and analyzed for cyclin D1 by western blot analysis. Exposure to collagen VI leads to much higher cyclin D1 levels. Panel D is a photograph of a western blot showing that collagen VI acts in part through NG2 in MCF-7 cells to stabilize cyclin D1. In the presence of increasing amounts of NG2 neutralizing antibody in the medium (0.15 μg/ml, 0.45 μg/ml, 0.75 μg/ml, 1 μg/ml), cyclin D1 levels decrease in a dose-dependent manner. Pre-immune antibodies, in contrast, do not affect the collagen VI induced increase. Results are shown as the MEAN±SEM in all cases.

FIG. 6 is micrographs and graphs showing breast tumor cell protein expression and activation differences between collagen VI +/+ and collagen −/− mice in the background of the MMTV-PyMT transgene. Panel A shows representative examples or laser capture microdissection used to isolate hyperplastic cells in a 100 µM radius from adipocytes, before (left micrograph) and after (left-center micrograph) removal of cells, and those MIN cells not associated at all with adipocytes (>500 µM from the nearest adipocyte); before (right-center micrograph) and after (right micrograph) removal of cells, from pathologically matched sections from mice carrying the MMTV-PyMT transgene in either a collagen VI +/+ or collagen VI −/− background. Panel B shows analysis of material from at least 8 independent areas pooled in each case. The material was used to make protein extracts that were spotted on protein arrays. The results shown were obtained from arrays of cells in close proximity to adipocytes. Arrays were probed with various antibodies against total and activated forms of proteins implicated in pro-oncogenic pathways. Panel C shows a quantitative comparison of ratio of phospho-specific protein to total protein from the protein arrays used in Panel B. Results are shown as the MEAN±SEM in all cases.

DETAILED DESCRIPTION OF THE INVENTION

Figure 2:
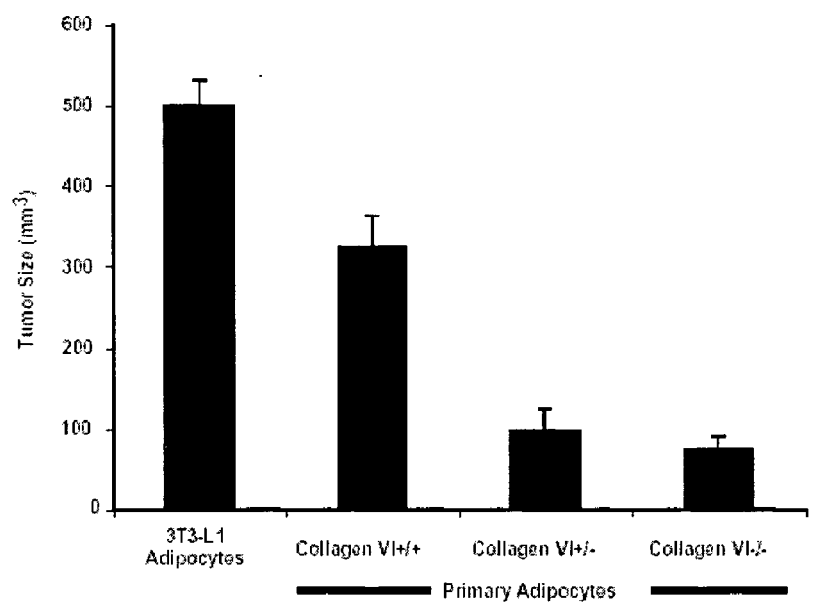
FIG. 2 is a graph showing that adipocytes from collagen VI +/− and collagen VI −/− mice are less potent stimulators of tumor growth in nude mice compared to those from collagen VI+/+ mice. $1 \times 10^5$ SUM159-PT cells were co-injected with the same number of isolated primary mammary adipocytes from collagen VI+/+, collagen VI +/−, collagen VI −/− mice or 3T3-L1 adipocytes into nude mice. Four weeks post injection, the sizes of the resulting foci were measured. n=4 mice in each cohort. Results are shown as the MEAN±SEM.

Accordingly, the inventors have developed various diagnostic and therapeutic methods based on their discovery that levels of the carboxy-terminal domain of collagen VIα3 dramatically accumulates in murine and human breast cancer lesions, and that the bound collagen VIα3 promotes survival and proliferation of the cells. See Example. As discussed therein, the relevant portion of collagen VI that accumulates in cancer lesions and promotes survival and proliferation of the cells is the carboxy terminal domain of collagen VIα3 and proteolytic fragments thereof.

Thus, in some embodiments, the invention is directed to methods of determining whether a cancer is progressing. The methods comprise determining whether cells of the cancer have more surface-bound collagen VIα3 than cancer cells that are not progressing.

These methods are expected to be useful for any cancer, especially carcinomas. In preferred embodiments, the cancer is breast cancer, colon cancer or ovarian cancer, due to the well-known upregulation of collagen VIα3 in those tissues. Preferably the cancer is breast cancer, especially breast cancer is of the ductal epithelia.

In these methods, the surface collagen VIα3 is preferably identified using an antibody, an antibody fragment, or an aptamer that specifically binds to collagen VIα3. As used herein, "antibody" includes the well-known naturally occurring immunoglobulin molecules from a monoclonal or polyclonal source from any vertebrate (e.g., mouse, chicken, rabbit, goat or human), as well as recombinant antibodies, including altered antibodies (e.g., humanized mouse). Antibody fragments preferably comprise a typical immunoglobulin antigen binding site (e.g., Fab or Fab2).

Aptamers are single stranded oligonucleotides or oligonucleotide analogs that bind to a particular target molecule, such as a protein or a small molecule (e.g., a steroid or a drug, etc.). Thus, aptamers are the oligonucleotide analogy to antibodies. However, aptamers are smaller than antibodies, generally in the range of 50-100 nt. Their binding is highly dependent on the secondary structure formed by the aptamer oligonucleotide. Both RNA and single stranded DNA (or analog), aptamers are known.

Aptamers that bind to virtually any particular target can be selected by using an iterative process called SELEX, which stands for Systematic Evolution of Ligands by EXponential enrichment. Several variations of SELEX have been developed which improve the process and allow its use under particular circumstances. See the references cited in PCT/US04/15752, all of which are incorporated by reference.

In preferred embodiments, the antibody, antibody fragment or aptamer is labeled with a detectable label. Nonlimiting examples include fluorescent labels, enzymes that are detected by addition of a substrate that is converted to a detectable product by the enzyme, and radioactive moieties such as $^{188}$Re. The tested cells can be from a biopsy, where the surface-bound collagen VIα3 is preferably detected using histology and light microscopy or with a cell sorter or cell counter. Alternatively, the tested cells can be detected in vitro, preferably using autoradiography or a gamma camera.

In other embodiments, the invention is directed to methods of identifying hyperplasia in a tissue. The methods comprise identifying epithelial cells of the tissue that have more surface-bound collagen VIα3 than epithelial cells not undergoing hyperplasia. In these embodiments, the identified epithelial cells are undergoing hyperplasia.

As in the methods described above, these methods can be used with any tissue. Preferably, the tissue is breast, colon or ovarian tissue, most preferably breast tissue. The tissue can be from a biopsy or in vivo. The surface collagen VIα3 is preferably identified using an antibody, an antibody fragment, or an aptamer that specifically binds to collagen VIα3. Preferably, the antibody, antibody fragment or aptamer is labeled with a detectable label and the surface-bound collagen VIα3 is detected using histology and light microscopy, a cell sorter or cell counter, or using autoradiography or a gamma camera.

Additionally, the invention is directed to methods of identifying carcinoma in a tissue. The methods comprise identifying epithelial cells that have more surface-bound collagen VIα3 than normal epithelial cells. In these embodiments, the identified epithelial cells are carcinoma cells.

As with the methods described above, these methods can be used with any tissue. Preferably, the tissue is breast, colon or ovarian tissue, most preferably breast tissue, such as breast cancer tissue of the ductal epithelia. The tissue can be from a biopsy or in vivo. The surface collagen VIα3 is preferably identified using a specific binding partner of the collagen VIα3, most preferably an antibody, an antibody fragment, or an aptamer. Preferably, the antibody, antibody fragment or aptamer is labeled with a detectable label and the surface-bound collagen VIα3 is detected using histology and light microscopy, a cell sorter or cell counter, or using autoradiography or a gamma camera.

The invention is further directed to methods of imaging carcinoma in a tissue. The methods comprise staining the tissue with a specific binding partner to collagen VIα3, then imaging epithelial cells of the tissue to determine whether the binding partner specifically binds to the epithelial cells. The epithelial cells comprising the specific binding partner are carcinoma cells.

In these embodiments, the specific binding partner preferably further comprises a detectable label. Alternatively, the specific binding partner is treated with a compound comprising a detectable label that specifically binds to the specific binding partner.

As with the methods described above, these methods can be used with any tissue. Preferably, the tissue is breast, colon or ovarian tissue, most preferably breast tissue, such as breast cancer tissue of the ductal epithelia. The tissue can be from a biopsy or in vivo. The surface collagen VIα3 is preferably identified using a specific binding partner of the collagen VIα3, most preferably an antibody, an antibody fragment, or an aptamer. Preferably, the antibody, antibody fragment or aptamer is labeled with a detectable label and the surface-bound collagen VIα3 is detected using histology and light microscopy, a cell sorter or cell counter, or using autoradiography or a gamma camera.

The invention is additionally directed to methods of treating a cancer. The methods comprise preventing binding of collagen VIα3 onto cells of the cancer. These methods can be used with any cancer, preferably breast, colon or ovarian cancer, most preferably breast cancer, such as of the ductal epithelia.

In some aspects of these methods, collagen VIα3 binding onto the cancer cells is prevented by exposing the cancer cells to an antibody, antibody fragment, or aptamer that specifically binds to collagen VIα3.

In other aspects of these methods, collagen VIα3 binding onto the cancer cells is prevented by exposing adipocytes near the cancer cells to an antisense molecule, a ribozyme, or an RNAi molecule that specifically inhibits translation of collagen VIα3 by the adipocytes. In these embodiments, the antisense nucleic acid, mimetic or ribozyme is expressed by a vector, for example a viral vector.

Preferred embodiments of the invention are described in the following Examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the Examples.

EXAMPLE 1

Example Summary

The interactions of transformed cells with the surrounding stromal cells are of importance for tumorigenesis and tumor progression. The relevance of adipocyte-derived factors for breast cancer cell survival and growth are well established. However, it remains unknown which specific adipocyte-derived factors are most critical in this process. Collagen VI is abundantly expressed in adipocytes. Collagen (−/−) null mice in the background of the MMTV-PyMT breast cancer model demonstrate dramatically reduced rates of early hyperplasia and primary tumor growth. Collagen VI signals its growthstimulatory and prosurvival effects in part through the NG2 chondroitin sulfate proteoglycan receptor expressed on the surface of malignant ductal epithelial cells to sequentially activate AKT, β-catenin, and stabilize cyclin D1. Levels of the carboxy-terminal domain of collagen VIα3, a proteolytic product of the full-length molecule, are dramatically upregulated in murine and human breast cancer lesions. In addition to promoting survival and proliferation, collagen VI may act locally to improve chemoresistance by upregulation of metallothioneins in mammary carcinoma cells. Therefore, adipocytes play a vital role in defining the extracellular matrix environment for normal and tumor-derived ductal epithelial cells and contribute significantly to tumor growth at early stages through secretion and processing of collagen VI.

Significance

There is an established link between increased adipose mass and elevated risk of cancer incidence, including breast malignancies. However, little insight has been gained so far in understanding the mechanistic contributions of adipocytes towards carcinogenesis. Here, we focus on the specific effects within the mammary microenvironment of the adipocyte-derived collagen VI and its contribution to early tumor progression. Collagen VI enhances tumor growth by providing pro-proliferative and pro-survival signals to the malignant ductal epithelial cells. Curtailing the local production of collagen VI and its cleavage products significantly reduces tumor growth and decreases chemoresistance. This study provides the first genetic evidence that stromal extracellular matrix protein can modulate tumor behavior, and offers a potential link between the epidemiological association of increased adipocyte mass and breast cancer.

Introduction

Here, we explored the bi-directional interactions between adipocytes and malignant ductal epithelial cells via the extracellular matrix (ECM). Using mice lacking the gene encoding the α1 chain of collagen VI that effectively gives rise to a functional null phenotype for holo-collagen VI (Bonaldo et al., 1998), we demonstrate that collagen VI promotes the development of hyperplastic foci and primary tumor growth, as judged by a markedly reduced rate of early hyperplasia/primary tumor growth in the collagen VI−/− null mice in the background of a breast cancer prone mouse strain (MMTV-PyMT). Collagen VI activates the pro-survival and proliferation pathways involving AKT, β-catenin, and cyclin D1 to achieve this effect. Use of laser capture microdissection and reverse phase protein arrays verifies this mechanism in vivo and illustrates the important role of adipocyte derived collagen VI in the process. Furthermore, collagen VI promotes chemoresistance in breast cancer cells through the induction of the metallothionein class of proteins. Immunohistochemistry, protein arrays and in vivo imaging studies argue for an important role for a collagen VIα3 carboxy-terminal proteolytic fragment during early tumor development. Combined, this suggests an important involvement of adipocyte-derived factors at early, but not at late stages of tumor progression.

Abbreviations used in this Example are as follows: chondroitin sulfate proteoglycan, CSPG; extracellular matrix, ECM; transforming growth factor, TGF; Dulbecco's modified Eagle medium, DMEM; fetal calf serum, FCS; sodium dodecyl sulfate, SDS; polyacrylamide gel electrophoresis, PAGE; protein kinase A, PKA; glycogen synthase kinase-3β, GSK-3β; adenomatous polyposis coli protein (APC); tris buffered saline, TBS; horse radish peroxidase, HRP; phosphate buffered saline, PBS; glycosaminoglycan, GAG; chondroitin sulfate, CS; Hematoxylin and Eosin, H&E; MMTV Polyoma Middle T transgenic, PyMT; mammary intraepithelial neoplasia, MIN; terminal duct lobular unit, TDLU; fibroblast growth factor, FGF.

Materials and Methods

Proteins and Reagents. DMEM (Dulbecco's modified Eagle's Medium) was prepared at the Albert Einstein Cancer Center Media prep facility. Human type VI collagen (99.9% homogeneity) was obtained from Research Diagnostics (Flanders, N.J.). Human collagen I was obtained from Collaborative Biomedical Products of Bedford, Mass. Collagen I and VI were used at a concentration of 30 μg/ml unless otherwise stated. The monoclonal antibody to β-catenin was obtained from Transduction Laboratories (Lexington, Ky.). A rabbit polyclonal α-collagen VI antibody specific to the C-terminal of the α3 subunit was generated using a bacterially produced GST-fusion protein raised against the last 70 amino acids of mouse collagen VIα3. A monoclonal α-collagen VI was obtained from Chemicon (Temecula, Calif.). The antibody against NG2 was a kind gift from Dr. Joel M. Levine, Department of Neurobiology and Behavior, SUNY at Stony Brook, Stony Brook, N.Y.

Cell Culture. 3T3-L1 cells were propagated and differentiated as described (Engelman et al., 1998). NIH-3T3 cells were grown and propagated in DMEM containing 10% donor calf serum and antibiotics. SUM-159PT cells were grown in 5% charcoal-stripped FCS, 10% Ham's F-12 nutrient medium, sodium bicarbonate, 10 mM HEPES, and 25 mM glucose (Flanagan et al., 1999). The SUM-159PT media was adjusted to pH 7.1. hTERT-HME1 cells were purchased from BD Biosciences (Franklin Lakes, N.J.) and grown as per manufacturer's instructions. Met-1 cells were a generous gift of Dr. Robert Cardiff (University of California, Davis, Calif.) and grown in 10% FCS-DME.

Immunoblotting. Separation of proteins by sodium dodecyl sulfate (SDS)-poly acrylamide gel electrophoresis (PAGE) fluorography, and immunoblotting were performed as previously described (Scherer et al., 1994). For western blots used to examine phosphorylated protein products, lysis buffer (TNET—1% Triton X-100, 150 mM NaCl, 5 mM EDTA pH 8.0, 50 mM Tris pH 8.0) was supplemented with 50 mM NaF, 30 mM sodium pyrophosphate, and 100 μM sodium orthovanadate.

Luciferase Assays. MCF-7 or SUM-159PT cells were seeded in 12-well plates sufficient to reach 50-60% confluency the next day. Two days prior to the luciferase readout, cells were transiently transfected with the TOPFLASH (contains 4 Tcf/Lef binding elements) luciferase promoter construct as well as a thymidine kinase driven renilla luciferase construct as a transfection control vector (Promega, Madison, Wis.) (Albanese et al., 2003). Superfect transfection reagent was used and for 12-well plates, 1.5 μg of DNA per well. Approximately 30 hours after the transfection, 30 μg/ml collagen I or VI was added to the cells for 12 hours. Subsequently, cells were processed using a dual-luciferase assay system for luciferase activity from both the TOPFLASH constructs and the renilla constructs. All results were standardized to the relative transfection efficiencies as observed from the renilla values.

Metabolic Labeling for β-catenin. MCF-7 cells, seeded in 6-well plates, were treated in methionine/cysteine deficient DMEM for 1 hour. Samples were pulsed with 500 μCi/ml [35S]-methionine/cysteine or [35S]-methionine/cysteine supplemented with either 30 μg/ml collagen I or VI for various time periods. After pulsing, the cells were washed with DMEM twice and lysed in a TNET buffer (100 mM phenylmethanesulfonyl fluoride and 60 mM octylglucoside). The lysates were cleared with Sepharose 4CL beads and subjected to β-catenin immunoprecipitation. The immunoprecipitates were electrophoresed on an SDS-PAGE gel, treated in 1M sodium salicylate for 30 minutes. Subsequently the gel was dried and exposed to film.

Microarray Analysis. MCF-7 cells at 60% confluency were treated with type VI or type I collagen for 7 hours. Total RNA was isolated by treatment with Trizol. Human microarrays (9596 spots) from the Albert Einstein College of Medicine were obtained and used for experimentation. Reverse transcription with the concomitant incorporation of Cy3 and Cy5 labeled nucleotides was performed on 100 μg of total RNA. The reverse transcribed RNA was incubated on the microarrays and subsequently analyzed using Scanalyze software as per the Albert Einstein College of Medicine standardized protocol (as described in Iyengar et al., 2003). Each independent experiment incorporated data from three separate chips and three separate RNA isolations as well as a reversal of the incorporated labeled nucleotides.

Tissue Recovery for Protein Microarray. Whole mammary tissue samples were recovered from MMTV Polyoma Middle T positive mice that were either in collagen VI wild type or knockout backgrounds. Mammary glands were removed and placed in cryomolds, covered with OCT (optimal cutting temperature compound), and immediately frozen in isopentane and stored at −80° C.

Sectioning and Staining. The OCT-embedded tissue blocks were cut with a Tissue Tek 2000 cryostat into 8 μm sections and placed onto plain, uncharged microscope slides. The frozen tissue section slides were stored at −80° C. until microdissection. Only one section was thawed and dissected at a time to minimize degradation of proteins. Frozen sections were submerged sequentially in 70% ethanol, deionized water, Hematoxylin (DakoCytomation, Glostrup, Denmark), Scott's Tap Water (blueing solution; FisherScientific, Pittsburgh, Pa.), 70%, 95%, and 100% ethanol for 10 seconds each with final dehydration for 10-30 seconds in Sub-X (Xylene Substitute Clearing Agent, SurgiPath, Richmond, Ill.). Protease inhibitors (Roche, Basel, Switzerland) were added to both the 70% ethanol and water solutions. The tissue section was air-dried prior to microdissection.

Murine Immunohistochemistry. Breast tumor tissues (MMTV-PyMT transgenic mice) were excised from mice euthanized with $CO_2$ and the tissues were fixed in 10% neutral-buffered formalin at room temperature overnight. The tissue was embedded in paraffin and 6-8 μm sections were made. The sections represented breast tumors from various stages in development, from adenomas to late stage carcinomas. An avidin-biotin-peroxidase staining system was used along with 3,3'-diaminobenzidine tetrahydrochloride as the chromogen. Sections were blocked to prevent non-specific binding with 10% horse serum, and the polyclonal collagen VI antibody was added to the sections and incubated in a humidified chamber at 4° C. overnight. Sections were washed twice in PBS between each incubation. Endogenous peroxidase was quenched with 3% $H_2O_2$ in methanol for 30 minutes at room temperature. A biotin-labeled α-rabbit secondary antibody was applied for 30 minutes at room temperature, followed by incubation with a preformed avidin-biotinylated enzyme complex for 30 minutes. Chromogen was subsequently added and cells were counterstained with Hematoxylin and Eosin (H&E) and the slides were mounted and examined by light microscopy.

Magnetic Resonance Imaging. All images were obtained using a 9.4-Tesla horizontal imaging system. Mice were anesthetized with isoflurane (1.5% in oxygen) delivered via a nose cone and were positioned in a 25 mm birdcage 1H coil. Body temperature was maintained with a homeothermic system. To quantitatively assess whole-body fat and water, each mouse was subjected to a 16-scan pulse-acquire sequence, and spectra, including the water and fat peaks, were obtained and integrated. For imaging, several data sets of nine slices of 1-mm thickness (gap between slices was 1 mm) spanning the whole body were obtained. Imaging was conducted using a routine spin-echo pulse sequence (18-ms echo time, 600-ms repetition time, and 2-signal averages per scan).

In vivo imaging of the carboxy-terminal domain of collagen VIα3. Pre-immune and collagen-specific polyclonal antibodies were radiolabeled directly with 188-Rhenium ($^{188}$Re) via reduction of antibody disulfide bonds with dithiothreitol (Dadachova and Mirzadeh, 1997). An amount of 2-4 mCi $^{188}$ReO$_4^-$ in saline was reduced by incubation with 20 mg Na gluconate and 20 μL 20 mg/mL SnCl$_2$ in 0.1 M HCl at 37° C. for 60 min. Reduced $^{188}$Re(V)-gluconate was combined with reduced and purified antibodies and kept at 37° C. for 60 min. Radioactivity not bound to the antibody was removed by centrifugal purification on Centricon-30 microconcentrators. Tumor-bearing mice were injected IP or IV with 0.5 mCi $^{188}$Re-Ab (100 μg). 1.5 h post-injection the animals were anesthetized with Isoflurane and scintigraphically imaged on Siemens LEM+ZLC™ DIGITRAC gamma camera equipped with a pin-hole collimator and ICON image-processing software.

Whole Mount Analysis. The fourth and fifth mammary glands of female mice were excised. The glands were maintained in a 75% acetic acid/methanol fixative for 4 hours. Subsequently, the sections were rehydrated in increasing percentages water to ethanol for 20 minutes and put in carmine red solution overnight. The samples were the treated with xylene, and photographs were taken. The area of early hyperplasia per gland was determined by using NIH Image J software.

Patients and Surgically Resected Frozen Tissues. The study set consisted of 45 primary human breast cancer cases, (6 of which had patient-matched normal and 1 which had both normal and premalignant cells available), 9 healthy controls taken from patients undergoing breast reduction surgery. The study was approved by the Institutional Review Boards of the National Cancer Institute and Georgetown University, Lombardi Cancer Center. All carcinomas were infiltrating ductal carcinomas.

Frozen sections were prepared for laser capture microdissection on plain glass microscope slides. Microdissection was performed with a PixCell II system (Arcturus Engineering, Mountain View, Calif.). Microdissected areas represented tumor only for the breast cancer cases, tumor or normal appearing mammary ducts adjacent to the tumor for the patient matched normal/tumor cases, or mammary ductal epithelium from the unaffected patients undergoing reduction mammoplasty.

Protein was extracted from the microdissected cells using 10 μl of extraction buffer per 1000 microdissected cells (1:1 dilution of 4% β-mercaptoethanol in 2× Tris-Glycine-SDS buffer (Invitrogen, Carlsbad, Calif.) with T-PER, tissue protein extraction liquid reagent (Pierce, Rockford, Ill.) for 1 hour at 70° C. After protein extraction, samples were boiled for 5 minutes and serial dilutions representing 1:1, 1:3 and 1:9 concentrations and a negative control were prepared in extraction buffer. 3 nl of the sample and control lysates were arrayed onto glass backed nitrocellulose slides (FAST slides, Schleicher & Schuell BioScience, Keene, N.H.) using a GMS 417 pin and ring style arrayer (Affymetrix, Santa Clara, Calif.). Arrays were treated with mild Reblot solution (Chemicon, Temecula, Calif.) for 15 minutes, washed twice for 5 minutes each, in 1×PBS without calcium or magnesium and blocked for a minimum of 30 minutes at room temperature with I-block protein block solution (Applied Biosystems, Foster City, Calif.).

Arrays were probed with antibodies to total and cleaved collagen VI antibodies using an automated slide stainer (DakoCytomation, Carpinteria, Calif.) with a catalyzed signal amplification system (DakoCytomation). A rabbit polyclonal α-collagen VI antibody specific to the C-terminal of the α3 subunit was generated using a bacterially produced GST-fusion protein raised against the last 70 amino acids of mouse collagen VIα3. A monoclonal α-collagen VI was obtained from Chemicon (Temecula, Calif.). Polyclonal primary antibody was used at the following final dilution: 1:1000. Monoclonal primary antibody was used at a final dilution of 1:250. One slide was stained for total protein with Sypro Ruby Protein Blot stain (Molecular Probes, Eugene, Oreg.) per manufacturer's instructions. The slide was imaged with an Alpha Innotek imager equipped with a Sypro Red/Texas Red filter. Exposure time was 20 seconds. Quantification of the relative pixel density of each array spot was performed with ImageQuant software version 5.2 (Molecular Dynamics, Piscataway, N.J.). Arrays were allowed to air dry and images were scanned on an Epson 1640SU flatbed scanner. Quantitation of the relative pixel density of each array spot was performed with ImageQuant software version 5.2 (Molecular Dynamics). Each intensity value was normalized to its total protein relative intensity value. The ratio of the spot intensity of the cleaved carboxy-terminal domain of collagen VIα3 to the full-length collagen VI transcript was calculated.

Laser Capture Microdissection and Protein Extraction for mouse samples. Microdissection was carried out using a Pixcell II and AutoPix Laser Capture Microdissection system (Arcturus Engineering, Mountain View, Calif.). Four areas were microdissected from the wild type phenotype frozen tissue sections, representing 34,000 cells. Ten areas were microdissected from the knockout phenotype tissue sections, representing 26,830 cells. Within each tissue section, only mammary tumor cells were microdissected. The microdissected samples were frozen at −80° C. until molecular analysis. Protein was extracted from the microdissected cells using 10 μl of extraction buffer per 1000 microdissected cells (1:1 dilution of 4% β-mercaptoethanol in 2× Tris-Glycine-SDS buffer (Invitrogen, Carlsbad, Calif.) with T-PER, tissue protein extraction liquid reagent (Pierce, Rockford, L) for 1 hour at 70° C.

Total Protein Blot Assay. One slide was stained for total protein with Sypro Ruby Protein Blot stain (Molecular Probes, Eugene, Oreg.) per manufacturer's instructions. The slide was imaged with an Alpha Innotek imager equipped with a Sypro Red/Texas Red filter. Exposure time was 20 seconds. Quantification of the relative pixel density of each array spot was performed with ImageQuant software version 5.2 (Molecular Dynamics, Piscataway, N.J.). Experiments were performed at the LCM Core facility of the National Cancer Institute.

Protein Biotinylation and Microarray. After protein extraction, samples were boiled for 5 minutes and serial dilutions representing 1:1, 1:2, 1:4, 1:8, 1:16 concentrations and a negative control were prepared in extraction buffer. A control lysate of activating anti-Fas (Upstate, Waltham, Mass.) treated Jurkat Cells was prepared in a similar manner. 3 nl of the sample and control lysates were arrayed onto glass backed nitrocellulose slides (FAST slides, Schleicher & Schuell BioScience, Keene, N.H.) using a GMS 417 pin and ring style arrayer (Affymetrix, Santa Clara, Calif.). Arrays were treated with mild Reblot solution (Chemicon, Temecula, Calif.) for 15 minutes, washed twice for 5 minutes each, in 1×PBS without calcium or magnesium and blocked for 30 minutes at room temperature with I-block protein block solution (Applied Biosystems, Foster City, Calif.).

Arrays were probed with antibodies to total and phosphorylated proteins using an automated slide stainer (DakoCytomation, Carpinteria, Calif.) with a catalyzed signal amplification system (DakoCytomation). Polyclonal primary antibodies were used at the following final dilutions: anti-Akt 1:250 (Cell Signaling Technology, Beverly, Mass.), anti-pAkt (ser 472/473/474) 1:250 (Becton Dickinson, San Diego, Calif.), anti-EGFR 1:50 (Cell Signaling Technology), anti-pEGFR (Y1068) 1:100 (Cell Signaling Technology), anti-GSK3β 1:200 (Becton Dickinson), anti-pGSK3β (ser9) 1:200 (Cell Signaling Technology), anti-ErbB2 1:100 (Cell Signaling Technology), anti-pErbB2 (Y1248) 1:1000 (Cell Signaling Technology), anti-pSTAT1 (Y701) 1:500 (Cell Signaling Technology), and anti-NFκB 1:100 (Cell Signaling Technology).

Biotinylated secondary antibody solution was used at the following final concentration: goat anti-rabbit IgG H+L 1:5000 (Vector Laboratories, Burlingame, Calif.). Chromogenic detection was with 3,3' diaminobenzidine tetrahydrochloride solution (DakoCytomation).

Image Analysis. Arrays were allowed to air dry and images were scanned on an Epson 1640SU flatbed scanner. Quantitation of the relative pixel density of each array spot was performed with ImageQuant software version 5.2 (Molecular Dynamics). Each intensity value was normalized to its total protein relative intensity value.

Results

The absence of collagen VI delays the onset of early hyperplasia. Northern blot analysis has previously shown that expression of collagen VI is highly enriched in adipose tissue and strongly induced during differentiation (Scherer et al., 1998). Immunohistochemistry and immunofluorescence show a strong positive signal for collagen VI protein on the surface of murine mammary adipocytes. Given the upregulation of collagen VI during tumor progression (Iyengar et al., 2003), we wanted to determine whether this upregulation is a secondary result of tumor growth or whether it has direct functional importance for tumor progression. To test a possible in vivo role of collagen VI, we opted to take advantage of MMTV-PyMT transgenic mice. To address the relevance of collagen VI, we crossed MMTV-PyMT mice with collagen VI−/− null mice (Bonaldo et al., 1998). Collagen VI−/− mice carry a genetic deletion in the α1 locus resulting in failure to secrete the a2 and a3 subunits and are functional knockouts for the entire collagen VI molecule. The initial characterization of these Col6α1−/− animals revealed no striking phenotypic changes except mild histological signs of myopathy in skeletal muscle of both homo- and heterozygous mutant animals (Bonaldo et al., 1998). This myopathy resembled pathologically Bethlem myopathy, a human inherited syndrome correlated with collagen VI genes (Jobsis et al., 1996a; Jobsis et al., 1996b; Speer et al., 1996). Subsequent characterization has revealed mitochondrial dysfunction and increased levels of apoptosis in myocytes of these mice (Irwin et al., 2003).

The mammary epithelium of PyMT transgenic mice in both the wildtype and collagen VI −/− null background were compared at 3-4 and 5-6 weeks. Whole mounts were generated from one set of inguinal mammary glands (4th) and H&E staining was performed on the corresponding contralateral glands. Early dysplastic foci representing mammary hyperplasia could be seen as early as 3-4 weeks in the PyMT+/ColVI+/+ mice (FIG. 1A). These foci occupied approximately five times the area of the dysplastic foci in the PyMT+/ColVI−/− null mice. The PyMT+/ColVI+/− mice exhibited levels of early hyperplasia closer to the PyMT+/ColVI+/+ mice than to the PyMT+/ColVI−/− mice. The differential levels of early hyperplasia are maintained through the 5-6 week time period when a similar 4-5-fold difference in area occupied by early dysplastic foci or mammary intraepithelial neoplasias (MINs) is observable (FIG. 1B). Importantly, there is less than a 10% difference in the number of foci counted at week 3 in PyMT+/ColVI+/+mice compared to PyMT+ColVI−/− mice (FIG. 1C). Hence, the actual number of transformed cells leading to foci is comparable, excluding unspecific effects on the PyMT antigen in a ColVI−/− background. There is however a dramatic difference with respect to the ability of the foci to proliferate and progress through tumorigenesis in the ColVI−/− background.

The whole mounts and H&E stained slides were subsequently examined as per the recommendations form the Annapolis meeting (Cardiff et al., 2000). At ~4 weeks, mammary glands from the knockout mice showed few small MINs involving the ducts and the terminal duct lobular units (TD-LUs) (FIG. 1D). These lesions are low grade and characterized by layers of atypical hyperchromatic epithelial cells with little cytoplasm. Some of the ducts showed surrounding fibrosis and inflammatory cells both in the wall and surrounding the involved ducts. The lesions seen in the PyMT+ColVI−/− mice were also present in the PyMT+ColVI+/+ and PyMT+ColVI+/− mice, though the lesions were more extensive in the latter two, in that they involved more ducts and TDLUs. In some of the more extensive lesions, MIN-involved ducts were filled with cells such that no lumen was apparent. The cells were of medium grade atypia with 4-7 mitotic figures per high-powered field. These lesions were multifocal. Histologically, the MIN lesions were seen as simple (semicystic bulges along the ducts containing one to several layers of atypical cells), solid (larger lesions containing dense masses of atypical cells in sheets), cystic (containing central fluid fluid-filled spaces, lined by multilayered epithelium that was frequently papillary), and "mixed" solid and cystic.

Collagen VI promotes primary tumor growth. The effects observed at early stages of tumor development are rather dramatic. To determine what the long-term consequences of the lack of collagen VI are on tumor growth, another cohort of PyMT+/ColVI+/+, PyMT+/ColVI+/−, and PyMT+/ColVI−/− mice were generated and primary tumor formation was monitored over 10 months. Both male and female PyMT+/ColVI+/+ mice exhibited quicker and more widespread induction of primary tumor development than PyMT+/ColVI−/− mice. In both males and females, PyMT+/ColVI+/− mice displayed an intermediate phenotype, suggesting a dose-dependent effect of collagen VI on tumor growth. PyMT+/ColVI+/+ mice had palpable tumors as early as 1 month, while PyMT+/ColVI−/− mice did not produce palpable tumors until 3 months (FIG. 1E). This difference in tumor size remained evident throughout the bulk of the observation period (10 months). The PyMT+/ColVI+/+mice exhibited tumors that were 4-6-fold larger, based on the three largest tumors in a given mouse, than those found in PyMT+/ColVI−/− mice. For instance, at month five, tumors in the ColVI+/+background females were on average 2488 mm$^3$±237 mm$^3$ in volume whereas those in the knockout background averaged 445 mm$^3$±27 mm$^3$ in size. Tumors in the heterozygote ColVI background were between the two averages but closer to wild type levels (FIG. 1F—left graph). Only by the latest stages (10 months), the tumors in the female PyMT+/ColVI−/− mice caught up in size and number with those in the PyMT+/ColVI+/+ mice. Results from the male transgenics displayed similar differences in patterns of tumor development (FIG. 1F—right graph). Importantly, PyMT+/ColVI+/+ and PyMT+/ColVI−/− mice were injected with an equal number (10$^5$) of metastatic tumor cells (Met1 cells) derived from an isogenic PyMT+ mouse. The number of lung metastases was determined at several time points after injection, and no difference in the number of lung metastases observed at any stage (data not shown). Therefore, the homing and growth of metastatic lesions is unaffected by the absence of collagen VI.

As an additional control, we examined murine breast ductal architecture to determine if the absence of collagen VI influences normal ductal development of the mammary tree. To assess this possibility, we examined whole mounts of knockout mammary glands at various stages of development (FIG. 1G). No striking differences can be observed between wildtype and null mice. Even though there may be a small reduction in the density of ductal branching in collagen VI −/− null female mammary glands adjacent to the lymph node (higher magnification) in the older regions of the structure, this is not observed in the rest of the mammary tree. This is further corroborated by a quantitative analysis, since there is statistically no significant difference in the number of terminal end buds in comparable regions of the mammary glands. In addition, there are no functional differences of mammary tissue between the genotypes, since collagen VI −/− mice are fully fertile, have normal litter sizes, lactate and have survival rates of pups comparable to wildtype.

Collagen VI-secreting adipocytes are more permissive to SUM-159PT growth in vivo. Given the dramatic reduction of tumor growth in collagen VI−/− null mice in the background of an MMTV-PyMT transgene, we wanted to assay the ability of collagen VI secreted from adipocytes to support mammary tumor growth independently. Athymic nude mice were injected with estrogen receptor negative SUM-159PT breast cancer cells (Flanagan et al., 1999) mixed with purified adipocytes isolated from collagen VI+/+, collagen VI+/− mice and collagen VI−/− null mice, 3T3-L1 adipocytes, or 3T3-L1 fibroblasts. For these experiments, primary adipocytes were prepared by collagenase digestion and all other stromal cell types were removed by centrifugation. This procedure yields a highly purified preparation of adipocytes. There was no difference in the level of structural integrity between wildtype and null adipocytes. Upon co-injection, tumors were allowed to grow for a period of 4 weeks. At the end of the experiment, tumor size was measured, the tumor mass was excised, and stained for the presence of the human ErbB2 antigen to confirm the presence of the human SUM-159PT cells. Primary Col VI+/+derived adipocytes and 3T3-L1 adipocytes best supported tumor growth and promoted the development of foci up to 300 mm$^3$ and 500 mm$^3$, respectively (FIG. 2). Adipocytes from either Col+/−mice or Col−/− mice supported foci only up to 100 mm$^3$. In line with our previously published results (Iyengar et al., 2003), 3T3-L1 fibroblasts had a minimal capacity to promote SUM-159PT foci formation in vivo.

Figure 3:
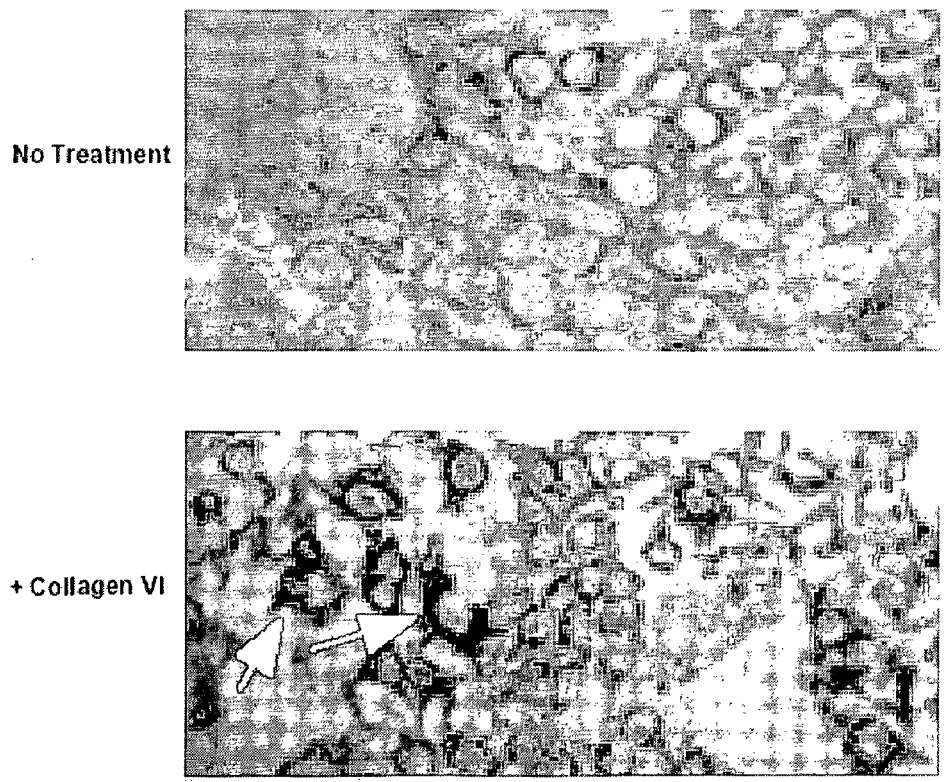
FIG. 3 is micrographs showing that collagen VI induces metallothionein in MCF-7 cells. MCF-7 cells were seeded onto glass coverslips and treated with vehicle (top panel) or collagen VI (30 μg/ml; bottom panel) in DME-BSA for five hours. At the end of the treatment, the cells were fixed and stained for metallothionein protein expression using immuno-histochemical procedures. The arrows indicate regions of high-level production of metallothionein.

Collagen VI induces genes associated with breast cancer progression, cAMP, and chemoresistance. In order to obtain a global perspective of transcriptional changes induced by type VI collagen in breast ductal epithelial cells, DNA microarray experiments were performed. To identify changes specifically brought about by collagen VI, we compared the collagen VI-induced transcriptional profile of MCF-7 cells with cells treated with collagen I. The cells were treated for six hours, total RNA was isolated and reverse transcribed and used to probe a ~9,500 human gene microarray. Collagen VI induced the upregulation of a host of genes that either promote tumorigenesis or that have been positively correlated with breast cancer in some other context. These genes include human transcription factor ETR101, growth factor PC4 homolog, protein tyrosine kinase tyk2, CDC28 protein kinase 1, and human metalliothionein-1f and -1e (Table 1). Notably, CDC28 protein kinase 1 promotes cellular proliferation via p27 Kip1 degradation, and metalliothionein-1f/1e is correlated with poor patient prognosis in breast cancer. In line with the mRNA data, collagen VI mediated the up-regulation of metallothionein also at the protein level as judged by immunohistochemistry in dB7 metastatic breast cancer cells treated with exogenous collagen VI protein (FIG. 3). Since metallothioneins are critically involved in cisplatin resistance, the observed upregulation of metallothionein by collagen VI provides for the first time a mechanistic explanation why cultivation of cisplatin-sensitive cells in the presence of collagen VI protein promotes cisplatin resistance (Sherman-Baust et al., 2003). In addition, collagen VI also specifically upregulated ATF3 and ATF4, transcription factors that are positive modulators of tumor development and invasion. Several other genes that promote angiogenesis, tumor growth, and/or tumor invasion were also found to be upregulated (Table 1). These genes include VEGF, calpain 4, IL-8, and angiopoietin-2.

TABLE 1

Collagen VI vs. Collagen I Driven Gene Induction Patterns in MCF-7 Cells - Microarray Analysis

| | | |
|---|---|---|
| EGR2 | Transcription Factor | UP 34.1 FOLD ± 5 |
| EST | Accession Number H77714 | UP 18.1 FOLD ± 2.3 |
| Metallothionein-1f | Metal Binding Protein; Consistently Up-regulated in Stage II and III Tumors; Associated with Tumor Invasion; Regulates p53 function | UP 18 FOLD ± 2.1 |
| Metallothionein-1e | Metal Binding Protein; Also Up-regulated in Late Stage Tumors; Regulates p53 function | UP 14 FOLD ± 1.7 |
| EST | Accession Number H54796 | UP 9.71 FOLD ± 3.7 |
| EST | Accession Number T50230 | UP 7.38 FOLD ± 2.6 |
| ATF3 | Promotes Tumor Metastic Potential and Malignancy | UP 6.81 FOLD ± 1.9 |
| ETR101 | Transcription Factor - no known function | UP 4.2 FOLD ± 0.75 |
| HSP90 | Chaperone | DOWN 2.25 FOLD ± 0.3 |
| Apolipoprotein C-III | | DOWN 3.31 FOLD ± 0.4 |

Collagen VI activates Tcf/Lef signaling downstream of GSK3β phosphorylation. Given the strong evidence for a direct involvement of collagen VI in early tumor growth, we wanted to gain a better understanding of the underlying molecular mechanism that leads to such a strong pro-proliferative and pro-survival/anti-apoptotic response in breast cancer cells. The PKB/Akt-GSK3β-β-catenin-Tcf/Lef pathway is relevant for tumorigenesis, both in colonic adenocarcinomas as well as in breast tumors (Michaelson and Leder, 2001). The activation of Tcf/Lef, the downstream effector in this signaling cascade, induces the transcription of various pro-oncogenes, including cyclin D1, NF-.B, cFOS, and ATF3 (Giles et al., 2003). Events that lead to the accumulation of β-catenin in the cytoplasm increase Tcf/Lef activity. We had previously demonstrated that collagen VI causes phosphorylation of GSK3β (Iyengar et al., 2003). PKA and Akt are known upstream kinases that target GSK3β for phosphorylation. The TOP FLASH reporter luciferase assay system was employed here to determine if collagen VI induced GSK3p phosphorylation led to downstream Tcf/Lef transcriptional activation in MCF-7 cells. Exposure to collagen VI caused a 6-8-fold induction of Tcf/Lef activity (FIG. 4A), whereas treatment with vehicle or addition of collagen I did not activate the Tcf/Lef transcriptional program.

Collagen VI prevents degradation of endogenous β-catenin in MCF-7 cells. Increased cellular β-catenin levels are a likely result from the observed increase in GSK3β phosphorylation and Tcf/Lef activity in breast cancer cells induced by collagen VI. To test this, β-catenin levels were monitored over the course of several hours after a pulse/chase reaction. Degradation of $^{35}$S-labeled β-catenin was evident in untreated cells, with decreased intracellular levels apparent as early as 0.5 to 1 hour followed by a further progressive decrease apparent by 2 hours. The presence of collagen VI dramatically reduced the rate of degradation and maintained levels of β-catenin over the course of the experiment (FIG. 4B). A marginal stabilization of β-catenin was also evident at early time points upon treatment with collagen 1, but increased degradation compared to collagen VI was evident after 2 hours. Collagen VI therefore specifically enhances intracellular β-catenin activity by decreasing its rate of degradation.

Collagen VI increases cyclin D1 protein stability through NG2/CSPG. Since cyclin D1 is a known target of Tcf/Lef and affected by GSK3β and β-catenin activity, we tested whether collagen VI could regulate cyclin D1 levels in breast cancer cells. MCF-7 cells were treated with vehicle, collagen VI or collagen I for five hours, and protein extracts were generated. Collagen VI indeed maintained and substantially increased cyclin D1 levels, whereas collagen I showed no significant change compared to the vehicle condition (FIG. 4C). A possible candidate to mediate these effects is the collagen VI receptor NG2/CSPG, a molecule that has previously been implicated as a growth mediator in a number of cancers (reviewed in Gladson, 1999). The role of NG2/CSPG in the context of breast cancer has however not been examined. We found that this receptor is prominently expressed in the normal mammary gland as well as in breast cancer cells (data not shown). A previously described neutralizing antibody preparation against NG2/CSPG was used to determine whether the collagen VI effects on cyclin D1 expression are indeed exerted through this receptor (Chekenya et al., 2002a; Chekenya et al., 2002b; Chekenya et al., 1999; Chen et al., 2002a; Chen et al., 2002b; Martin et al., 2001; Ughrin et al., 2003). MCF-7 cells pretreated with the αNG2/CSPG antibody were exposed to collagen VI protein, and cyclin D1 levels were monitored. Increasing concentrations of the αNG2/CSPG antibody in the presence of collagen VI led to progressively lower levels of intracellular cyclin D1 (FIG. 4D). Antibody treatment in the absence of added collagen VI had no effect on cyclin D1 stability. Pre-treatment with a non-specific control antibody preparation prior to collagen VI exposure did not impair the collagen VI mediated stabilization of cyclin D1. This suggests that collagen VI mediates its effects on intracellular cyclin D1 levels at least in part through binding to and activation of the cell surface receptor NG2/CSPG.

Figure 5:
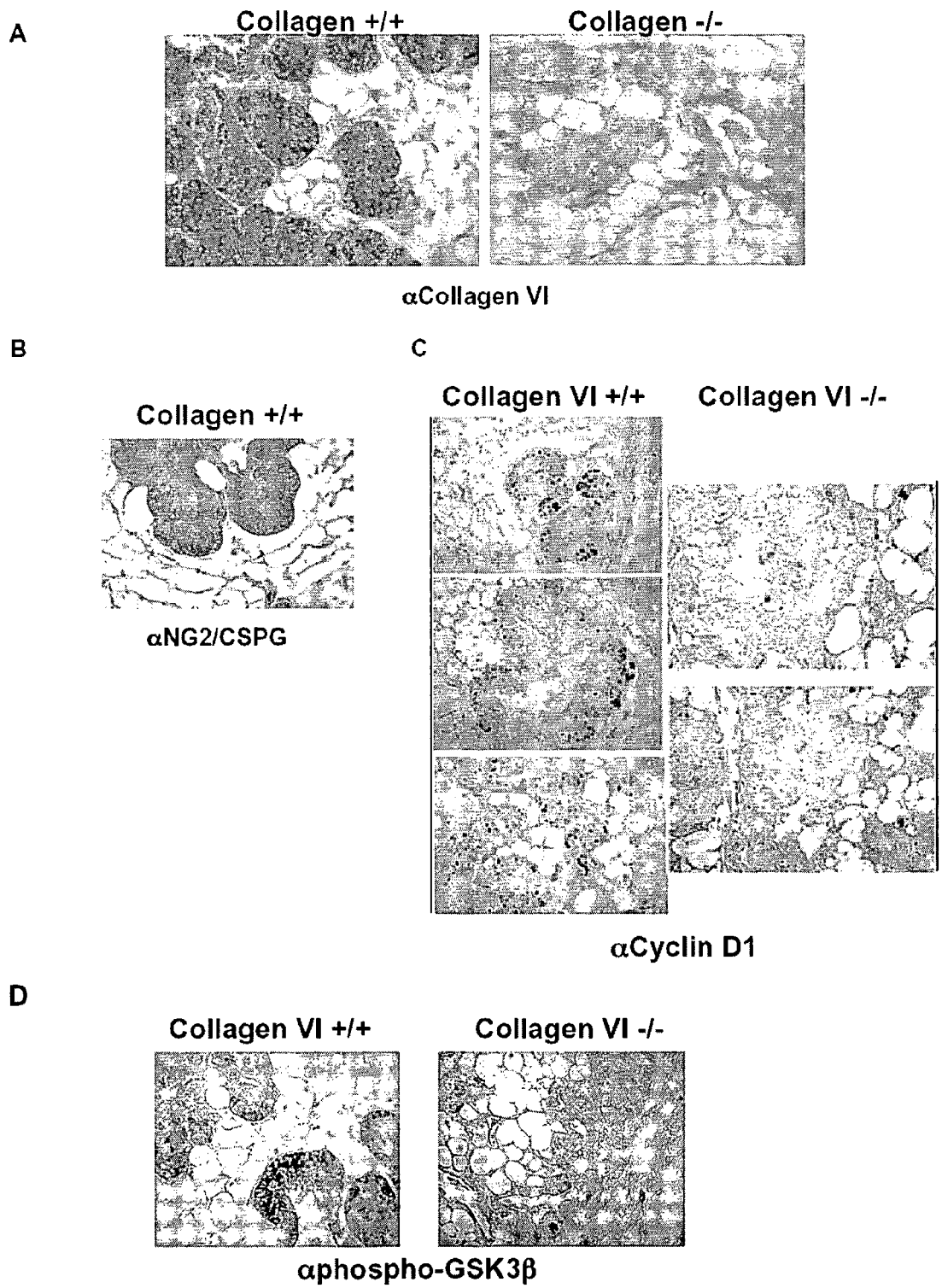
FIG. 5 is micrographs of an immunohistochemical analysis of pathologically matched tumors from collagen (+/+) and collagen (−/−) mice in the MMTV-PyMT background. Panel A shows the absence of collagen Vα3 signal in collagen (−/−) mice by staining for collagen VIα3 (with carboxy-terminal polyclonal antibody) on mammary sections taken from pathologically matched hyperplasias developed in collagen (+/+) and collagen (−/−) mice. An intense stain for collagen VIα3 can be observed in the wildtype background, whereas no signal is detected in the knock out. Note that the most intense stain is observed in malignant regions. Panel B shows that NG2/CSPG is expressed at highest levels in malignant regions adjacent to adipocytes. NG2/CSPG was stained on a section taken from a hyperplastic area of a collagen VI (+/+) mouse carrying the MMTV-PyMT antigen. Panel C shows that cyclin D1 is expressed at highest levels in malignant regions adjacent to adipocytes. Cyclin D1 was stained in pathologically matched hyperplasias from collagen (+/+) and collagen (−/−) mammary tissues of mice carrying the MMTV-PyMT transgene. Very little staining for cyclin D1 is observed in collagen (−/−) mice. Panel D shows that GSK3β is activated at highest levels in malignant regions adjacent to adipocytes. Phospho-GSK3β was stained in pathologically matched hyperplasias from collagen (+/+) and collagen (−/−) mammary tissues of mice carrying the MMTV-PyMT transgene. Very little staining for phospho-GSK3β is observed in collagen (−/−) mice.

Immunohistochemical evidence for adipocyte-enriched collagen VI effects on GSK3β and cyclin D1. To lend further support to our in vitro observations, we examined sections of hyperplasia and primary tumors by immunohistochemistry. Staining for the carboxy-terminus of collagen VIα3 in PyMT+/ColVI+/+ mice was localized to the periphery of the tumor masses, appearing in a ring pattern around the region of early hyperplasia, and around the periphery of adipocytes (FIG. 5A). A gradient in collagen staining was observed with increased staining of MIN cell peripheries closer to adipocytes. Staining on the interior of regions of early hyperplasia showed weaker collagen VI staining. No collagen VI staining was observed in PyMT+/ColVI−/− mice. Immunohistochemical staining for NG2/CSPG demonstrated localization to cell surfaces throughout the tumor masses in both PyMT+/ColVI+/+ and PyMT+/ColVI−/− mice (FIG. 5B). The staining was notably more pronounced on the surfaces of tumor cells closer to the adipocyte-rich regions. When staining for cyclin D1, we observed a ring of malignant cells on the outside of the MIN regions that exhibited positive staining in PyMT+/ColVI+/+ mice, similar to the pattern that was recently reported by Pollard and colleagues (Lin et al., 2003). This ring of cyclin D1 staining was reduced, however, in pathologically matched PyMT+/ColVI−/− mice (FIG. 5C). The staining pattern for phosphoGSK3β was similar to that for cyclin D1 (FIG. 5D). A gradient was again seen with increased staining intensities closer to adipocytes on the leading edges of the hyperplastic lesions. Staining was present in matched PyMT+/ColVI−/− tumors, though the levels were substantially reduced.

Collagen VI activates a similar pathway in vivo as in vitro. In light of the effects of collagen VI on the generation of dysplastic foci and growth of primary tumors, we wanted to gain a further understanding as to which signaling pathways critically contribute towards this phenotype in vivo. Laser capture microdissection was employed to isolate specific cells prior to reverse phase protein array analysis. Specimens of stage and size-matched early malignancies isolated from PyMT+/ColVI+/+, PyMT+/ColVI+/−, and PyMT+/ColVI−/− mice were analyzed. Cells were chosen from clusters located at the periphery of the hyperplasias in close juxtaposition to adipocytes and from clusters more distal to adipocytes (FIG. 6A). Proteomic reverse phase array analysis revealed highly significant differences that demonstrate the variable activation states of a number of relevant signaling modules in the presence and absence of collagen VI (FIG. 6B). Most notably, while total Akt levels were comparable in PyMT+/ColVI+/+ and PyMT+/ColVI−/− derived cells, a much larger portion of the protein was phosphorylated/activated in PyMT+/ColVI+/+ mice. Similarly, a greater percentage of GSK3β, IκB, and ErbB2 are phosphorylated in MIN cells of PyMT+/ColVI+/+ mice compared to pathologically matched hyperplasias in PyMT+/ColVI−/− mice. While not investigated in vitro herein, both STAT1 and NF-κB (p52) exhibited increased expression, phosphorylation and activation (STAT1) in PyMT+/ColVI−/− hyperplastic cells. Finally, though there were slightly increased levels of the activated MAP Kinase ERK in hyperplasias from knockout animals, there were far greater levels of total ERK in these same cells. This results in an overall lowered activation state of ERK in these knockout mice (FIG. 6C). Perhaps most importantly, the differences in the activation state of all of these signaling components between PyMT+/ColVI+/+ and PyMT+/ColVI−/− derived cells were only observed near the periphery of the tumor in proximity to adipocytes, whereas no significant differences in signaling could be observed in cells isolated from the center (not shown).

Figure 7:
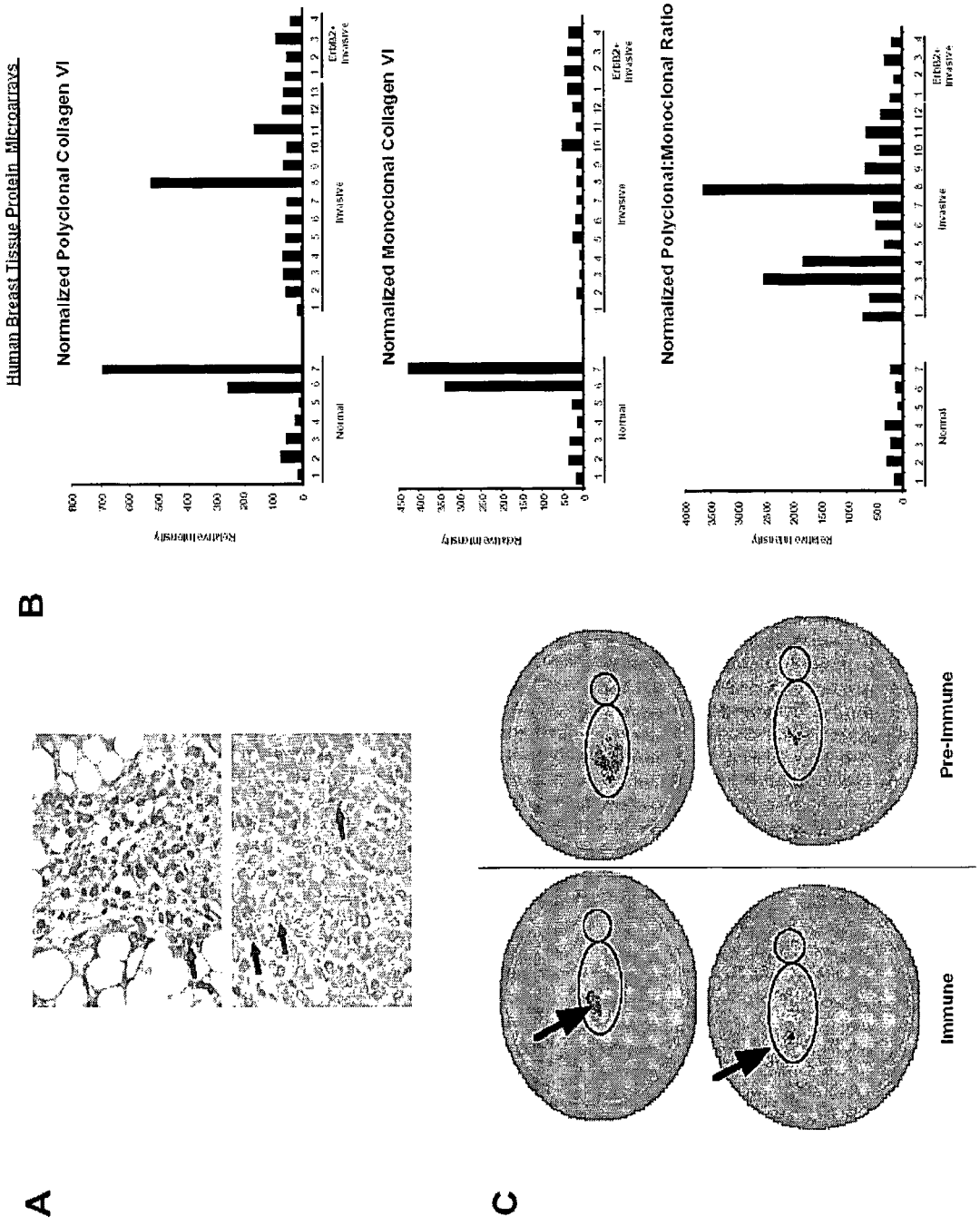
FIG. 7 shows micrographs and graphs showing increased levels of the C-terminal domain of collagen VIα3 In tumor cells in the proximity of adipocytes compared in human mammary tumor sections Panel A shows high levels of the carboxy-terminal domain of collagen VIα3 in a human mammary tumor sample. The top panel indicates significant levels of collagen VI staining around human breast carcinoma cells near the vicinity of the adipocytes. The bottom panel shows reduced staining in tumor cells more distantly located from a cluster of adipocytes in the same tumor. Panel B shows the polyclonal to monoclonal ratio of collagen VI expression. Reverse phase protein arrays where used to determine levels of the C-terminal domain from collagen VIα3 (top graph) and the full-length collagen VI protein (middle graph) found in normal and tumor tissue of human cancer specimens. The bottom graph shows the ratio of relative signals obtained for polyclonal and monoclonal antibodies, indicating a clear bias to higher relative levels of the α3 C-terminal domain in most tumor tissues examined. Panel C shows that the carboxy-terminal fragment of collagen VIα3 accumulates on the surface of tumors. Polyclonal IgGs from immune and nonimmune preparations against the carboxy-terminal domain of collagen VIα3 were isolated and radiolabeled with 188-Rhenium. Preparations were injected either intraperitoneally (top) or intravenously by tail vein injection (bottom) into MMTV-PyMT mice carrying tumor (10 weeks of age). The outline of the mouse is indicated. Mice were imaged on a Siemens LEM+ZLC™ DIGITRAC gamma camera.

Human breast tumor specimens display collagen VI staining similar to the pattern observed in mice. We have previously reported increased staining for collagen VI during progression of tumorigenesis in the mouse (Iyengar et al., 2003). To test whether these observations are relevant for human disease, we probed human tumor and normal human mammary tissue sections with two different antibody preparations: a polyclonal antibody raised against the carboxy-terminal domain of the collagen VIα3 subunit and a commercially available monoclonal antibody against collagen VI that recognizes another, not defined epitope on one of the other α chains. Normal mammary glands exhibited relatively low levels of collagen VI staining with both antibodies, with a predominant signal detectable around adipocytes (data not shown). Late stage carcinomas, however, showed a very intense staining pattern for collagen VI around the tumor masses when using the antibody directed against the carboxy-terminal domain of the collagen VIα3 subunit (FIG. 7A). Immunostaining was particularly prominent in tumor cells near adipocytes, and less pronounced in cells more distantly located from adipocytes. Interestingly, a direct comparison of the staining pattern obtained with the monoclonal antibody recognizing the full-length collagen complex (diffuse stain around adipocytes) with the polyclonal antibody against the carboxy-terminal domain (enhanced stain around tumor cells) shows a differential staining pattern (not shown). This strongly suggests that the α3 carboxy-terminal domain may have been cleaved from the polymeric remainder of the collagen VI. Furthermore, this small soluble domain may in turn be the only portion of collagen VI that is directly interacting with tumor cells and points to the α3-carboxy-terminal domain as a potentially relevant factor for cancer progression.

Collagen VI regulation in the human mammary carcinoma. The potential importance of collagen VI protein may be as an early diagnostic marker of mammary hyperplasia or as growth promoting factor that can be inhibited to reduce tumor progression. To that end, we undertook experiments to look at collagen VI protein expression in normal and tumor cells from human cancer patients with various stages of the disease by using reverse phase protein microarrays. Both the polyclonal antibody against the collagen VIα3 domain was used as well as the monoclonal antibody against the collagenous domain of the full-length protein. Interestingly, the relative levels of the collagen VIα3 carboxy-terminal domain (FIG. 7B, top panel) compared to the levels of the full-length collagen VI protein (FIG. 7B, middle panel) were strongly biased towards the collagen VIα3 domain in tumor, but not in healthy tissue as judged by the ratio of the signal intensities obtained with the two different antibodies (FIG. 7B, bottom panel). This suggests that the relative ratio of the collagen VIα3 carboxy-terminus to full-length collagen VI may serve as a useful diagnostic marker, even in human specimens. Interestingly, this observation did not hold up for ErB2 positive tumors.

In vivo imaging of tumors with antibodies recognizing the carboxy-terminal domain of collagen VIα3. In order to gain a systemic overview as to the relative abundance/enrichment of the carboxy-terminal domain of collagen VIα3, we isolated polyclonal IgGs from immune and non-immune preparations and radiolabeled them with 188-Rhenium. Preparations were injected either intraperitoneally (FIG. 7C top) or intravenously by tail vein injection (FIG. 7C bottom) into an established murine breast cancer model, a transgenic mouse expressing the Polyoma Middle T antigen under the control of the MMTV promoter (MMTV-PyMT) (Guy et al., 1992). These mice were subsequently imaged on a gamma camera. While the pre-immune IgGs rapidly accumulated in the kidneys, the immune IgGs specifically accumulated on the tumor mass, suggesting that the carboxy-terminal domain of collagen VIα3 is highly enriched on the surface of tumors cells and may serve as a potent biomarker for breast tumor cells.

Discussion

The extracellular matrix affects breast ductal epithelial cells at multiple levels. It is important during development of the ductal architecture, by influencing cell morphology, and modulating proliferation through direct action on ductal epithelial cells as well as by acting as a reservoir for circulating growth factors. Under normal conditions, the basement membrane forms an effective barrier between the ductal epithelium and the surrounding stromal cells. Upon neoplastic transformation, the ductal cells break through the basement membrane and are subsequently in direct contact with a new extracellular milieu. Adipocytes, the most abundant cell type in the stroma, are highly active endocrine cells that not only secrete a host of soluble factors, but also contribute very significantly towards the rather unique make up of the extracellular matrix. Our previous work characterized the effects that the entire complement of soluble secretory products from adipocytes exerts on ductal epithelial cells on survival and growth (Iyengar et al., 2003). Here, we have focused on the role of an abundant, adipocyte-enriched extracellular matrix component, type VI collagen and implicate collagen VI both genetically and biochemically for the first time in the pathophysiology of breast cancer.

The upregulation of collagen VI observed during murine tumor progression suggested that collagen VI has the potential to influence breast cancer progression in vivo. Our genetic evidence, derived from the analysis of PyMT+/ColVI+/+, PyMT+/ColVI+/−, and PyMT+/ColVI−/− null mice, strongly supports the involvement of collagen VI in the development of dysplastic foci, the promotion of tumor growth. This PyMT model characteristically develops rapid yet pathologically relevant spontaneous mammary adenocarcinomas (Cardiff et al., 2000; Lin et al., 2003). The collagen VI−/− null mouse has previously been characterized and displays physiological changes that are limited to the destabilization of muscle fibers that results in a low level myopathy. It is unlikely that such a muscle-associated phenotype plays an indirect role in this breast cancer model. A very recent study shows that collagen VI null myocytes have increased susceptibility to pro-apoptotic stimuli that results in mitochondrial dysfunction (Irwin et al., 2003). The absence of collagen VI did not have an effect on the number of dysplastic foci observed as measured by MINs and TDLUs. No other systemic effects were observed. However, early hyperplasia and primary tumor growth was dramatically reduced in the absence of collagen VI.

The effect of collagen VI on primary tumor growth was investigated in both female and male mice. Male mice develop mammary adenocarcinomas at a slower rate, which allows for a more accurate assessment of growth over time. The female mouse model, however, is more relevant to human breast cancer. The reduced rate of tumor growth in males compared to females may in part be related to the lower amount of local adipose tissue. Loss of adipose tissue at later stages of tumor development (using aP2-DPT transgenic mice that ablate adipocytes at 80-100 days of life in the background of the MMTV-PyMT transgene), does not alter tumor development, growth, or metastasis (data not shown). These findings suggest that adipocytes are important in the early, but not late development of tumors.

Reconstitution studies were used to further examine if collagen VI is necessary for tumor development. 3T3-L1 adipocytes (an established adipocyte cell line) and isolated primary adipocytes that secrete collagen VI both supported tumor foci formation and growth in co-injection experiments with SUM-159PT cells. Those adipocytes lacking collagen VI, isolated from collagen VI (−/−) null mice, were unable to sustain tumor growth to the same extent. The reconstitution study further demonstrates that collagen VI is a critical factor secreted by adipocytes, promoting dysplasia and early tumor growth in vivo.

An important issue is how collagen VI manages to exert these pro-mitogenic/pro-survival effects on breast cancer cells. Consistent with the role of collagen as a soluble paracrine factor, released by adipocytes and acting upon adjacent tumor cells, we show by immunohistochemistry that murine mammary hyperplasias express NG2/CSPG, a previously characterized collagen VI receptor. However, a role for additional receptors for collagen VI, such as integrin $\alpha_2\beta_1$, cannot be excluded, particularly in light of the fact that our previously published microarray studies that examined transcriptional changes induced by the total complement of secretory proteins in cancer cells showed that integrin $\alpha_2\beta_1$ is significantly upregulated upon exposure to adipocyte-conditioned medium (Iyengar et al., 2003). Nevertheless, the reduction of collagen VI-mediated signaling in breast cancer cells (decreased cyclin D1 stabilization) using neutralizing antibodies against NG2 suggests that NG2 is a major player in the context of breast tumor growth and collagen VI. The NG2/CSPG receptor has not previously been demonstrated to promote the phosphorylation of GSK3β or activate the downstream Wnt pathway to regulate cyclin D1. In MCF-7 cells, we found that collagen VI, deviating from several other ECM proteins, uniquely promotes Tcf/Lef activity and inhibits β-catenin degradation. Therefore, collagen VI derived from adipocytes can induce a pro-mitogenic signaling cascade downstream of the NG2/CSPG receptor, using relatively well-established pathways in breast cancer cells to stabilize β-catenin, thereby elevating Tcf/Lef activity, which in turn upregulates cyclin D1. The effect of collagen VI on breast cancer cells is not limited to MCF-7 cell lines, as our in vivo data has suggested.

Immunohistochemistry of dysplasic foci and primary tumors revealed staining patterns that reflected the in vitro findings. Collagen VI was found in a gradient from adipocytes to breast cancer cells. The NG2/CSPG receptor displayed a similar expression gradient. Furthermore, relative expressions of phosphoGSK3β and cyclin D1 in the presence of collagen VI, compared to the absence of collagen VI, resembled those found in MCF-7 cells under similar conditions. These results argue that the promotion of dysplasia and tumor growth by collagen VI may occur by the same mechanism as illustrated by our in vitro studies. At later stages, the PyMT model generates malignant tumors that lead to metastases. Collagen VI did not have an effect on the number of metastases found. Collagen VI activity through NG2/CSPG, therefore, is likely to be involved in early tumor growth. Subsequently, upon reaching primary tumor stages and metastatic potential, the tumor cells lose their dependence on collagen VI.

Proteomic data derived from PyMT+ColVI+/+, PyMT+ColVI+/−, and PyMT+ColVI−/− mice supported our in vitro data. The most striking difference was seen in the activation of Akt in malignant cells close to adipocytes expressing collagen VI. There was a sharp gradient with respect to the activation state of the pro-survival factors in the hyperplastic cells adjacent to collagen VI null adipocytes. The increased phosphorylation of Akt suggests that Akt may be the dominant kinase responsible for the phosphorylation of GSK3β in vivo. Nonetheless, the remainder of the Tcf/Lef pathway shows similar responses in vitro and in vivo. The changes in phosphorylation in GSK3β and ErbB2 induced by collagen VI are consistent with increased proliferation and tumor progression. Decreased total STAT1 protein and STAT1 phosphorylation/activation in the presence of collagen VI reflects a reduction in apoptotic signals in wild type backgrounds (Boudny and Kovarik, 2002). A similar reduction in pro-apoptotic signal is seen with elevated IκB phosphorylation in PyMT+/ColVI +/+tumor bearing mice. While the collagen VI-mediated down-regulation of NF-κB is associated with increased apoptosis, this study did not examine nuclear translocation or the ubiquitin pathway, both of which are involved in NF-κB-induced responses. Therefore, the role of NF-κB in this system remains to be better understood.

Detailed proteomic analysis using immunohistochemistry provides additional insight into the role of collagen VI. The presence of collagen VI leads to upregulated cyclin D1 expression. Hyperplasic cells near the periphery of MINs, which are closer to adipocytes, express higher levels of cyclin D1 than those closer to the middle of MINs. Correspondingly, cells on the periphery of the tumor have been found to be more proliferative than those at the core, further emphasizing the importance of adipocyte factors including collagen VI in tumor proliferation. Also, in agreement with the in vitro signaling data, there was increased staining for pGSK3β on the leading edge of tumor cells in the PyMT +/ColI+/+ mice whereas matched tumors from collagen VI (−/−) mice stained very poorly for the pGSK3β molecule.

Microarray data from MCF-7 cells treated with soluble collagen VI demonstrated gene induction patterns consistent with the activation of a number of genes associated with breast cancer growth and progression. Perhaps the most intriguing result involved the observation that collagen VI induces several members of the metallothionein class of genes. Metallothionein, a critical intracellular metal binding protein, has been implicated as a pro-tumorigenic molecule that has the capacity to render cells more chemoresistant. A recent report highlighted the role of collagen VI in promoting chemoresistance in ovarian cancer cells (Sherman-Baust et al., 2003). However, the underlying mechanism for the increased resistance to cisplatin treatment was not worked out in these studies. It is quite possible that collagen VI along with its potent mitogenic and survival characteristics may also be important in promoting chemoresistance through the induction of metallothioneins.

Immunohistochemistry of human mammary carcinoma tissue reveals strong collagen VI staining around the tumor masses, focused primarily around the adipocytes and producing a gradient similar to that seen in murine sections. Normal human mammary tissue exhibits low-level collagen VI staining. These results demonstrate collagen VI protein presence in human breast tumors. While these results do not define collagen VI as a critical factor in the development and proliferation of human tumors, the strong upregulation of collagen VI expression in human malignant lesions combined with the highly provocative mouse data suggests that collagen VI may be relevant for human breast cancer as well.

Several independent lines of evidence point towards the potential importance of the collagen VIα3 carboxy terminal domains in modulating the protein's activity. Published observations described that a proteolytic cleavage event that releases this fragment can indeed occur upon secretion of the holo-collagen VI complex (Aigner et al., 2002). The resulting cleavage product is soluble and may be the fragment that has a high affinity for the surrounding breast cancer cells. Consistent with such a conclusion is the observation that only antibodies to this carboxy-terminal domain display a highly significant increase in staining intensity in immunohistochemical slides during tumor progression. Antibodies recognizing other domains on collagen VI display the expected staining pattern primarily surrounding adipocytes with little signal detected on the tumor cells directly.

The degree of accumulation of the carboxy-terminal fragment during tumor progression represents systemically a specific event, since radiolabeled antibodies against this domain rapidly concentrate on the surface of tumor cells with very little additional systemic accumulation as judged by our in vivo imaging of tumor-bearing mice with a radiolabeled antibody. This highlights the potential of the collagen VIα3 C-terminus to serve as a sensitive in vivo marker that may have significant diagnostic potential. It is apparent from our proteomic array studies on human breast tumor extracts that the carboxy-terminal domain and the full length collagen VI protein are detected at different relative levels, depending whether normal or transformed human breast tissue is examined. The increased C-terminal fragment to full-length collagen VI ratio may be therefore be a potent a prognostic indicator. Future studies on a much larger number of specimens will have to address the general usefulness of this ratio with respect to prediction of future disease outcome and whether neutralization of the carboxy-terminal domain of collagen VIα3 fragment through the use of specific antibodies may serve as a therapeutic modality for early stage breast cancer therapy in humans.

Supplemental Data

Figure 8:
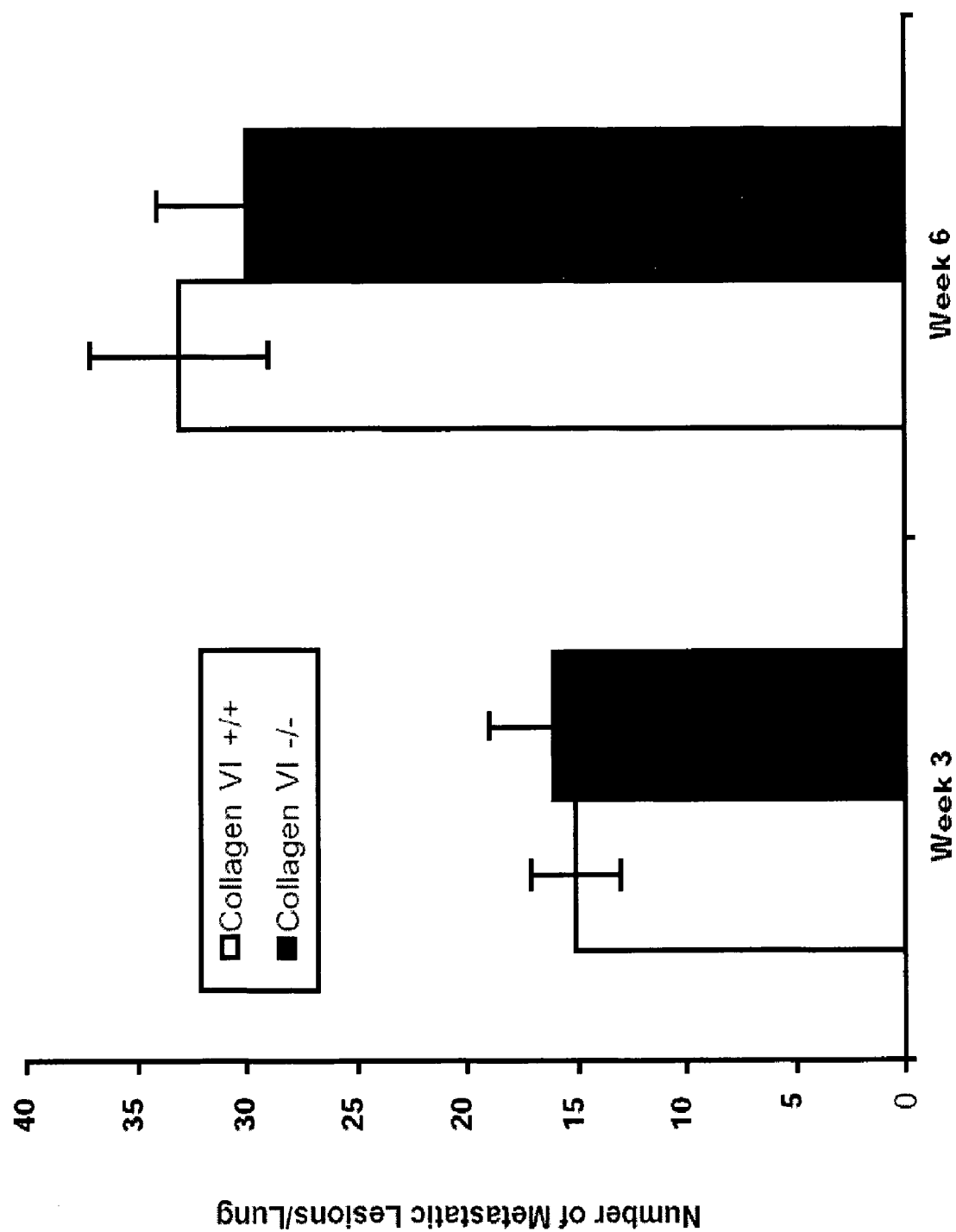
FIG. 8 is a graph showing that collagen VI −/− mice do not display a reduced number of metastatic lesions. $1 \times 10^5$ Met1 cells were tail vein injected into 5 mice per group of either wild type collagen +/+ (white bars) or collagen VI −/− mice (black bars). Mice were sacrificed at 1, 2, 3, 4, and 6 weeks post injection. Lungs were subsequently inflated and fixed in formalin for H&E staining. The metastatic lesions were counted.

Collagen VI does not affect the formation of metastases in other tissues. Given that collagen VI promotes hyperplasia and primary tumor development, we sought to determine if collagen VI promoted metastasis. PyMT+/ColVI+/+ and PyMT+/ColVI−/− mice were injected with an equal number ($10^5$) of metastatic tumor cells (Met1 cells) derived from an isogenic PyMT+ mouse. Lung is one of the most prominent tissues for metastatic growth of breast cancer cells. Therefore, the number of lung metastases was determined after 1, 2, 3, 4, and 6 weeks. None of the time points examined showed a difference in the number of lung metastases observed ($p>0.05$), suggesting that the homing and growth of metastatic lesions is unaffected by the absence of collagen VI (FIG. 8). This is consistent with the observation that lung tissue does not display a particularly prominent expression for collagen VI under normal conditions. Breast tumor cells, once they achieve strong metastatic potential, may therefore no longer critically depend on collagen VI for growth. This conclusion is supported by recent observations that suggest an up-regulation of collagen VIα3 subunit only in primary, non-metastatic tumors (Wang et al., 2002).

Figure 9:
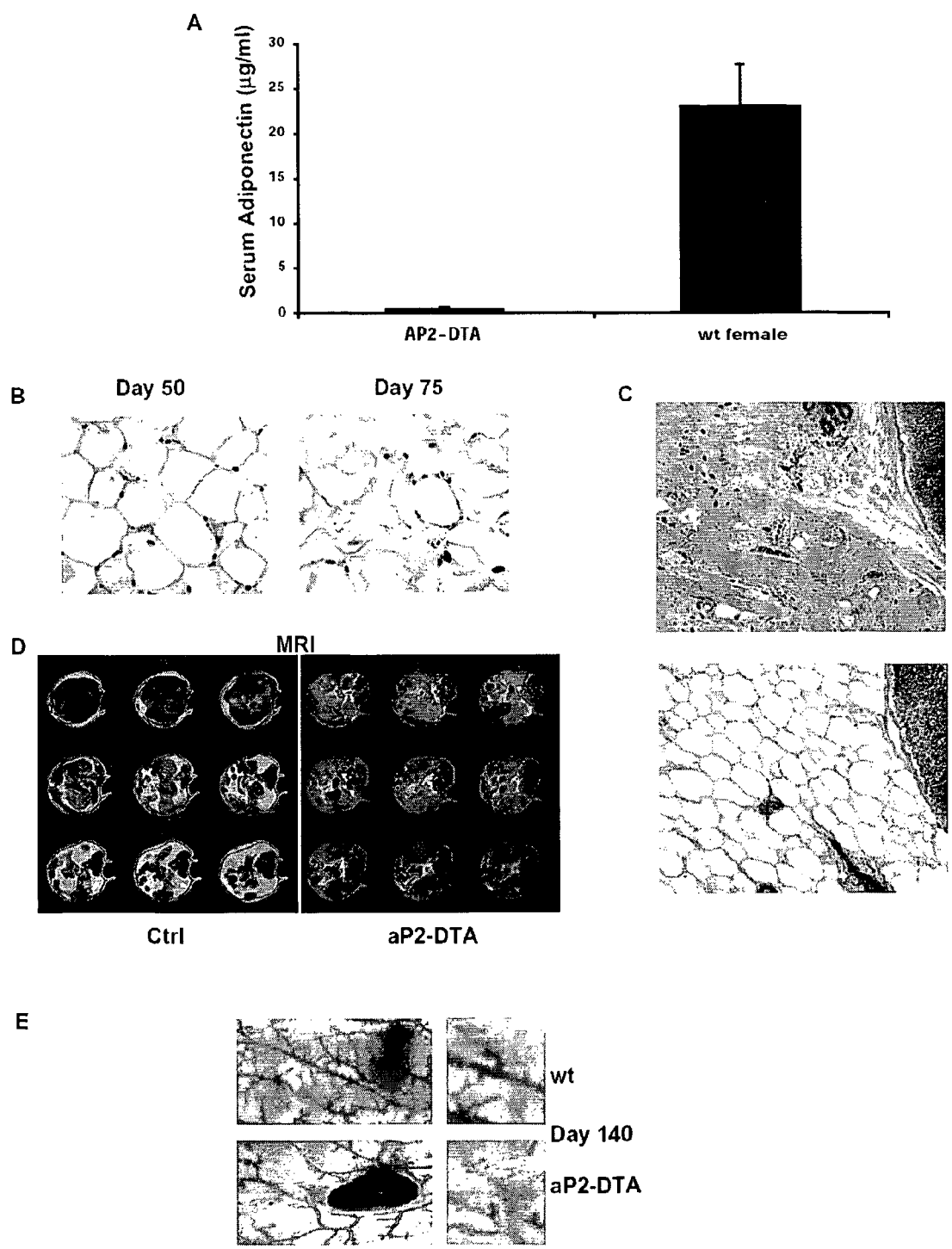
FIG. 9 is a graph, micrographs and MRI scans showing that a model of late onset lipoatrophy, the aP2-DTA mouse, does not display reduced tumor growth. Panel A shows ablation of adipocyte-derived serum markers. Levels of the adipocyte-secreted protein adiponectin in the serum of 140 day old aP2-DTA mice was compared to wildtype littermates. n=5. Panel B shows that the aP2-DTA transgene ablates adipocytes around 10 to 12 weeks of age. H&E was used to stain mammary fat pad sections taken from aP2-DTA mice at 50 days of age (just prior to fat loss) and 75 days of age (during fat ablation). Panel C shows the absence of morphologically distinct adipose tissue at late age. Mammary sections were taken from aP2-DTA mice (358 days old; top) and an age-matched wild type (bottom) littermate. Note the complete absence of adipose tissue at this stage. Panel D shows a lack of adipose tissue as judged by MRI imaging. MRI images were made of wild type and aP2-DTA mice (140 days old). Transverse sections of the abdomen are shown. Fat appears white in the images. Panel E shows that a lack of adipose tissue does not significantly alter the ductal epithelial structure. Whole mounts of mammary glands were taken from wild type and aP2-DTA mice (140 days old mice; low and high magnifications are shown). Panel F shows that late stage fat loss does not affect number of foci or primary tumor size. The graphs show the number of lesions (left graph) and primary tumor sizes (right graph) from MMTV-PyMT mice transgenic mice (white bars) or MMTV-PyMT/aP2-DTA double transgenic at 13 weeks of age (lesions) and 13 and 16 weeks of age (primary tumor size). n=5. Panel G show that late stage fat loss does not affect number of metastatic lesions. MMTV-PyMT mice transgenic mice (white bars) or MMTV-PyMT/aP2-DTA double transgenic at 10, 13 and 16 weeks of age were analyzed for the number of metastatic lesions found in lungs. n=5. Panel H is an H&E stain of lung lesions showing no pathologic difference in type of metastases found in the presence or absence of adipose tissue post primary tumor development.

Late stage tumor growth and formation of metastases no longer critically depends on adipose tissue. The previous results indicate that the collagen VI−/− mice displayed an equally high susceptibility to metastatic spread and growth. This suggests that the tumor cells lose their dependence on the local presence of collagen VI for survival and growth once they become metastatic. In order to test whether this phenomenon is not restricted to collagen VI but can be generalized to other adipocyte-derived factors, we chose a genetic model for late stage loss of adipose tissue. Overall, our aim was to assess how relatively late stage tumor progression was affected by the lack of adipocytes and their secreted factors in the local microenvironment. Transgenic mice expressing low levels of diphtheria toxin under the control of the adipocyte-specific aP2 promoter display normal adipose tissue development (Ross et al., 1993). These mice completely lose their adipocytes between 15 to 20 weeks of age as judged by a dramatic reduction of the adipose-specific secretory factor adiponectin in circulation (FIG. 9A). The female transgenic fatless mouse has normal ductal development and can reproduce without problem. Even several months after the onset of adipose tissue loss, the overall architecture of the breast ductal epithelium remains intact (FIG. 9B). By day 80, however, a loss in some adipocyte membrane integrity can be observed (FIG. 9B), and at later stages, adipose tissue has morphologically completely disappeared (FIG. 9C). FIG. 9D represents magnetic resonance images taken of the DPT+ and wild type transgenic mice, illustrating how effectively adipose tissue mass has been reduced and almost completely eliminated at about 20 weeks post birth. The ductal architecture remained preserved after the loss of adipocytes (FIG. 9E).

This transgenic line was crossed into the MMTV-PyMT line. The relatively late onset of fat loss allows the primary tumors to fully develop under conditions similar to the local environment in a wildtype mouse. Indeed, primary tumor growth in aP2-DpTx/MMTV-PyMT mice was comparable to mice carrying the MMTV-PyMT transgene after 80 days (FIG. 9F). The aP2-DpTx/MMTV-PyMT double-transgenic mice allow us to answer the question as to whether primary tumors that have grown beyond early hyperplasia still require the sustained presence of adipose tissue-derived factors for further progression and metastases. Work from a number of laboratories suggests that early hyperplasias require mammary fat pads to form foci and progress through tumorigenesis. However, cell lines and transplanted mammary ducts that have progressed to increased levels of malignancy are not as strictly dependent upon this adipose-rich microenvironment (MacLeod et al., 2002). Consistent with these observations, once adipose tissue is ablated in the aP2-DpTx/MMTV-PyMT double-transgenic mice (FIG. 9E), we failed to observe a difference in the rate of foci formation, primary tumor expansion, and growth compared to MMTV-PyMT littermates that do not lose the adipose tissue (FIG. 9F). In addition, loss of adipose tissue had no effect on the number, size, and histological grade of metastases to the lungs (FIG. 9G, H).

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A method of identifying hyperplasia in a tissue, the method comprising identifying epithelial cells of the tissue that have more surface-bound collagen VIα3 carboxy-terminus than full length collagen VI protein, wherein the epithelial cells of the tissue that have more surface-bound collagen VIα3 carboxy-terminus than full length collagen VI protein exhibit hyperplasia, and wherein the surface-bound collagen VIα3 carboxy-terminus is identified using an antibody that specifically binds to collagen VIα3 carboxy-terminus or an antigen-binding fragment that specifically binds to collagen VIα3 carboxy-terminus.

2. The method of claim 1, wherein the tissue is breast, ovarian or colon tissue.

3. The method of claim 1, wherein the tissue is breast tissue.

4. The method of claim 1, wherein the tissue is from a biopsy.

5. The method of claim 1, wherein the surface collagen is identified using an antibody that specifically binds to collagen VIα3 carboxy-terminus.

6. The method of claim 1, wherein the surface collagen VIα3 is identified using an antigen-binding fragment that specifically binds to collagen VIα3 carboxy-terminus.

7. The method of claim 5, wherein the antibody is labeled with a detectable label.

8. The method of claim 1, wherein the surface-bound collagen VIα3 is detected using histology and light microscopy.

9. The method of claim 1, wherein the surface-bound collagen VIα3 is detected using a cell sorter or cell counter.

10. The method of claim 1, wherein the cells with bound collagen VIα3 is detected using autoradiography or a gamma camera.

11. A method of identifying carcinoma in a tissue, the method comprising identifying epithelial cells that have more surface-bound collagen VIα3 carboxy-terminus than full length collagen VI protein, wherein epithelial cells of the tissue that have more surface-bound collagen VIα3 carboxy-terminus than full length collagen VI protein are carcinoma, and wherein the surface-bound collagen VIα3 carboxy-terminus is identified using an antibody that specifically binds to collagen VIα3 carboxy-terminus or an antigen-binding fragment that specifically binds to collagen VIα3 carboxy-terminus.

12. The method of claim 11, wherein the carcinoma is breast, ovarian or colon cancer.

13. The method of claim 11, wherein the carcinoma is breast cancer.

14. The method of claim 11, wherein the tissue are from a biopsy.

15. The method of claim 11, wherein the surface collagen is identified using an antibody that specifically binds to collagen VIα3 carboxy-terminus.

16. The method of claim 11, wherein the surface collagen is identified using an antigen-binding fragment that specifically binds to collagen VIα3 carboxy-terminus.

17. The method of claim 15, wherein the antibody is labeled with a detectable label.

18. The method of claim 11, wherein the surface-bound collagen VIα3 is detected using histology and light microscopy.

19. The method of claim 11, wherein the surface-bound collagen VIα3 is detected using a cell sorter or cell counter.

20. The method of claim 11, wherein the cells with bound collagen VIα3 is detected using autoradiography or a gamma camera.

* * * * *